(12) United States Patent
Zheng et al.

(10) Patent No.: US 9,095,542 B2
(45) Date of Patent: Aug. 4, 2015

(54) MODIFIED SODIUM-MONTMORILLONITE, PREPARATION METHOD AND USES THEREOF

(75) Inventors: Haihui Zheng, Zhejiang (CN); Guanglie Lv, Zhejiang (CN); Zhiguo Xia, Zhejiang (CN); Nian Xu, Zhejiang (CN); Sheng Le, Zhejiang (CN); Zhongchao Ma, Zhejiang (CN); Yufeng Chi, Zhejiang (CN); Wenbo Chen, Zhejiang (CN); Jixin Chen, Zhejiang (CN)

(73) Assignee: HAILISHENG PHARMACEUTICAL CO., LTD, Lincheng, Zhoushan, Zhejiang (CN)

( * ) Notice: Subject to any disclaimer, the term of this patent is extended or adjusted under 35 U.S.C. 154(b) by 145 days.

(21) Appl. No.: 13/143,830

(22) PCT Filed: Jan. 8, 2010

(86) PCT No.: PCT/CN2010/000032
§ 371 (c)(1),
(2), (4) Date: Sep. 26, 2011

(87) PCT Pub. No.: WO2010/078833
PCT Pub. Date: Jul. 15, 2010

(65) Prior Publication Data
US 2012/0003328 A1    Jan. 5, 2012

(30) Foreign Application Priority Data
Jan. 8, 2009    (CN) .......................... 2009 1 0001369

(51) Int. Cl.
| | |
|---|---|
| *C04B 14/10* | (2006.01) |
| *C04B 35/628* | (2006.01) |
| *A61K 33/12* | (2006.01) |
| *B82Y 30/00* | (2011.01) |
| *C01B 33/40* | (2006.01) |
| *C09C 1/42* | (2006.01) |
| *B01J 39/14* | (2006.01) |
| *B01J 20/10* | (2006.01) |
| *B01J 20/12* | (2006.01) |
| *B01J 20/28* | (2006.01) |

(52) U.S. Cl.
CPC .................. *A61K 33/12* (2013.01); *B01J 20/10* (2013.01); *B01J 20/12* (2013.01); *B01J 20/28007* (2013.01); *B01J 39/14* (2013.01); *B82Y 30/00* (2013.01); *C01B 33/40* (2013.01); *C09C 1/42* (2013.01); *C01P 2002/72* (2013.01); *C01P 2004/62* (2013.01); *C01P 2004/64* (2013.01); *C01P 2006/80* (2013.01); *Y10T 428/2982* (2015.01)

(58) Field of Classification Search
USPC .......................................................... 424/123
See application file for complete search history.

(56) References Cited

U.S. PATENT DOCUMENTS

| | | | | |
|---|---|---|---|---|
| 3,693,412 A | * | 9/1972 | Kalousek | ..................... 73/54.23 |
| 2006/0057171 A1 | | 3/2006 | Kim et al. | |

FOREIGN PATENT DOCUMENTS

| | | |
|---|---|---|
| CN | 1957948 A * | 5/2007 |
| CN | 101002796 A | 7/2007 |
| CN | 101016157 A | 8/2007 |
| CN | 101272986 A | 9/2008 |
| CN | 101602509 A | 12/2009 |
| WO | 2007/090355 A1 | 8/2007 |

OTHER PUBLICATIONS

Chen Zhiyong, Chemical Engineer, 2002, 5, 17, 18 and 25, ISSN 1002-1124.*
Translation of Chen Zhiyong, Chemical Engineer, 2002, 5, 17, 18 and 25, ISSN 1002-1124.*
Chen et al., Espacenet Machine Translation of CN1957948, May 9, 2007.*
Chen Zhiyong; "Studys on the Preparation Methodology with Acidification of Sodium Base Betontte", Chemical Engineer, Oct. 2002, No. 5, pp. 17,18 and 25, ISSN: 1002-1124 Machine Translation.
International Search Report: mailed Apr. 15, 2010; PCT/CN2010/000032.
Chen Zhiyong; "Studies on the Process of Preparing Sodium Base Bentonite by Acidification", Chemical Engineer, vol. 92, No. 5, Oct. 2002; 11 pages.

* cited by examiner

*Primary Examiner* — Misook Yu
*Assistant Examiner* — Kauser M Akhoon
(74) *Attorney, Agent, or Firm* — Ladas & Parry LLP

(57) ABSTRACT

Provided are a modified Na-montmorillonite and a preparation method thereof, wherein the content of $Na^+$ in the modified sodium-montmorillonite, calculated as $Na_2O$, is not less than 2.0%. The modified Na-montmorillonite has more reasonable microstructure, higher performance, and better quality. Also provided are a method for preparing a modified nanometered Na-montmorillonite from the modified Na-montmorillonite, and the modified nanometered Na-montmorillonite obtained by the method. Also provided are uses and a pharmaceutical composition of the modified Na-montmorillonite or modified nanometered Na-montmorillonite.

6 Claims, 6 Drawing Sheets

MODIFIED SODIUM-MONTMORILLONITE, PREPARATION METHOD AND USES THEREOF

TECHNICAL FIELD

The invention relates to a process for preparing a modified sodium-montmorillonite, and to a modified sodium-montmorillonite prepared by such process and its uses.

BACKGROUND OF THE INVENTION

Chinese patent applications CN200610054632.1 and WO2007090355A, CN200610055117.5 and CN200680028247.8 (WO2007051427A), CN200610005685.4 and CN2008101096824 have disclosed respectively "process for purification of montmorillonite, purified montmorillonite and composition thereof", "modified montmorillonite, process for preparing the same and uses thereof", "use of nanomontmorillonite in manufacture of medicaments and pharmaceutical combinations thereof" and "a process for purifying montmorillonite by means of electrophoresis, montmorillonite prepared by such process and uses thereof". These patent applications respectively use the process of purification, modification, nano-treatment or electrophoretic treatment to remove impurities in bentonite, in order to improve the microstructure and performance of montmorillonite, enhance its quality and widen the application field of bentonite, in particular to widen significantly the medical use of montmorillonite and enhance its therapeutic effect. Montmorillonite, however, needs to be further improved in terms of its quality and microstructure in order to produce better effect.

SUMMARY OF THE INVENTION

One object of the present invention is to provide a new type of modified sodium-montmorillonite, characterized in that the $Na^+$ content (calculated as $Na_2O$) in the modified sodium-montmorillonite is not less than 2%, preferably not less than 3%, more preferably not less than 4%, and most preferably not less than 5%.

Another object of the present invention is to provide a process for preparing a modified sodium-montmorillonite, comprising 1) mixing a montmorillonite with a purity of not less than 90% and 0.1-10 mol/L of an acid in a weight ratio of 1:1-100 for the acidification or acid treatment of the montmorillonite, followed by adding 0.05-3.5% of an dispersing agent based on the weight of the montmorillonite, boiling the mixture to remove the acid and washing to give a liquid dispersion of modified hydrogen-montmorillonite;

2) controlling the solid content of the liquid dispersion of the modified hydrogen-montmorillonite obtained from 1) at 0.5-10% and adding an sodium modification agent in an amount of not less than the cation exchange capacity of the montmorillonite in order to subjecting the montmorillonite to sodium modification.

Another object of the present invention is to provide a modified nanometered sodium-montmorillonite, characterized in that the $Na^+$ content (calculated as $Na_2O$) in the modified nanometered sodium-montmorillonite is not less than 2%, preferably not less than 3%, more preferably not less than 4%, and most preferably not less than 5%.

Another object of the present invention is to provide a process for preparing a modified nanometered sodium-montmorillonite, comprising the following steps: preparing an aqueous solution of the modified sodium-montmorillonite according to the present invention with a solid content of 0.5-60%; dispersing and homogenizing the aqueous solution by high-speed shearing effect in, for example, high-speed shearing machine, high-speed disperser, ball mill or high pressure homogenizer; drying; and pulverizing.

The invention also relates to the use of the modified sodium-montmorillonite or the modified nanometered sodium-montmorillonite in the manufacture of medicines.

In addition, the present invention relates to the use of the modified sodium-montmorillonite or the modified nanometered sodium-montmorillonite for preventing and treating digestive tract diseases and a pharmaceutical composition comprising the same.

The present invention also relates to the use of the modified sodium-montmorillonite or the modified nanometered sodium-montmorillonite in the manufacture of adjuvant of medicines or foods and in the fields of petroleum industry, construction, pesticide, fertilizer and the like.

DRAWINGS OF THE INVENTION

DETAILED DESCRIPTION OF THE INVENTION

Figure 1:
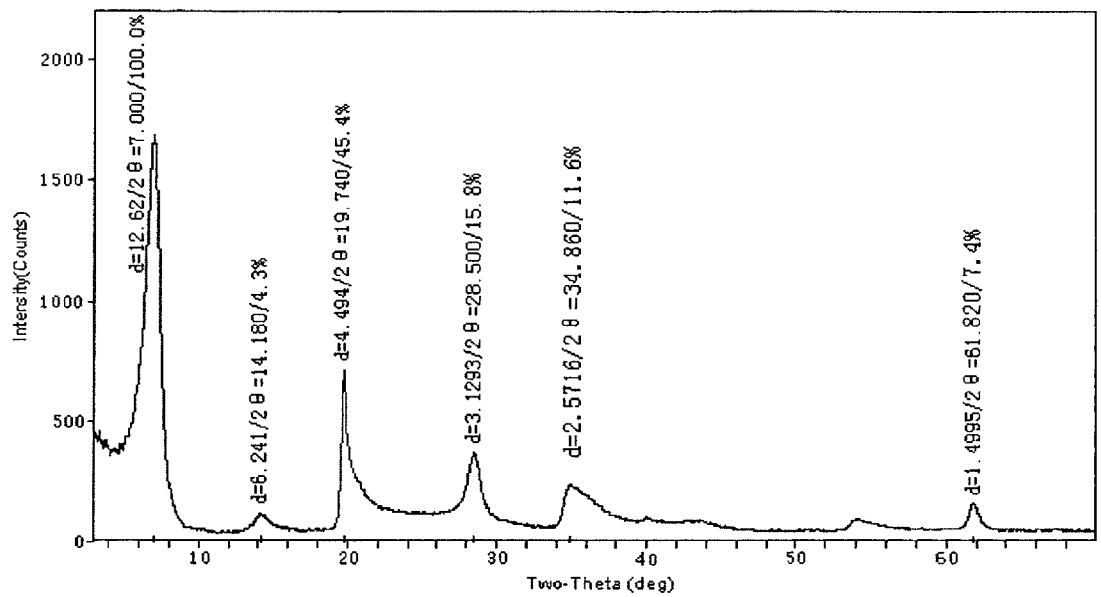
FIG. 1 is an X-ray powder diffraction spectrum of the modified sodium-montmorillonite B-1 prepared in example 1.

One object of the present invention is to provide a new type of modified sodium-montmorillonite, characterized in that the $Na^+$ content (calculated as $Na_2O$) in the modified sodium-montmorillonite is not less than 2%, preferably not less than 3%, more preferably not less than 4%, and most preferably not less than 5%.

In a preferred embodiment of the present invention, the value of d corresponding to $d_{002}$ peak in the X-ray powder diffraction spectrum of the modified sodium-montmorillonite is 5.50 Å-7.00 Å, preferably 5.75 Å-6.75 Å, more preferably 6.00 Å-6.5 Å, and most preferably 6.25 Å.

In a preferred embodiment of the present invention, the $Ca^{2+}$ content (calculated as CaO) in the modified sodium-montmorillonite is not more than 1%, preferably not more than 0.5%, more preferably not more than 0.1%, and most preferably not more than 0.05%.

In a preferred embodiment of the present invention, the thixotropic index of the modified sodium-montmorillonite is not less than 1, preferably not less than 2, more preferably not less than 3, and most preferably not less than 4.

In a preferred embodiment of the present invention, the purity of the modified sodium-montmorillonite is not less than 97%, preferably not less than 98%, more preferably not less than 99%, and most preferably not less than 99.5%.

In a preferred embodiment of the present invention, the cation exchange capacity (CEC) of the modified sodium-montmorillonite is 90-150 mmol/100 g, preferably 100-145 mmol/100 g, more preferably 110-140 mmol/100 g, and most preferably 115-135 mmol/100 g.

In a preferred embodiment of the present invention, the swelling capacity of the modified sodium-montmorillonite is not less than 7.0 ml/g, preferably not less than 9.0 ml/g, more preferably not less than 10.0 ml/g, and most preferably not less than 12.0 ml/g.

In a preferred embodiment of the present invention, the adsorption of strychnine sulfate by per gram of the modified sodium-montmorillonite is 0.30-0.75 g, preferably 0.40-0.70 g, more preferably 0.45-0.65 g, and most preferably 0.50-0.60 g.

In a preferred embodiment of the present invention, the content of heavy metal in the modified sodium-montmorillonite is not more than 10 ppm, preferably not more than 7 ppm, more preferably not more than 5 ppm, and most preferably not more than 3-4 ppm.

In a preferred embodiment of the present invention, the impurity level of the modified sodium-montmorillonite is not more than 3%, preferably not more than 2%, more preferably not more than 1%, and most preferably not more than 0.5%.

In an exemplary embodiment, the modified sodium-montmorillonite according to the present invention is prepared by the following steps: purified montmorillonite, as the raw material, is acidified and washed for several times, by which the montmorillonite is effectively freed from the cation between the ion layers (i.e. calcium ion, hydrogen ion or magnesium ion) and acid-soluble impurities, resulting in a modified hydrogen-montmorillonite, and at the same time the stacking layers of the montmorillonite are opened and decrease in thickness so that the α-quartz embedded in the montmorillonite layers is exposed and removed by physical methods to give a purified modified hydrogen-montmorillonite; then the modified hydrogen-montmorillonite is subjected to sodium modification to give a modified sodium-montmorillonite, which is subsequently freed from base-soluble impurities by washing (membrane separation technique) by virtue of the good suspendability of the modified sodium-montmorillonite and the large difference of specific gravity between modified montmorillonite and unmodified montmorillonite.

The modified sodium-montmorillonite according to the invention has more appropriate microstructure, better performance and quality, higher $Na^+$ content between layers, better therapeutic effect and wider therapeutic application. Compared with natural sodium-montmorillonite, natural calcium-montmorillonite (such as Smecta), and the modified sodium-montmorillonite prepared in CN200610055117.5 and CN200680028247.8 (WO2007051427A), the modified sodium-montmorillonite according to the invention has the following properties:

1. The modified sodium-montmorillonite according to the invention has higher purity, lower impurity content, larger cation exchange capacity, significantly higher $Na^+$ content between layers, and better hydration swelling property;

2. The modified sodium-montmorillonite according to the invention has thinner stacking layers of structural unit layers and thus better suspendability, dispersibility and thixotropy, and significant gelation property. For example, the modified sodium-montmorillonite according to the invention can form gel-like substance with net-like structure and thixotropy in artificial gastric juice and artificial intestinal juice.

The present invention provides a process for preparing a modified sodium-montmorillonite, comprising 1) mixing montmorillonite with a purity of not less than 90% and 0.1-10 mol/L of an acid in a weight ratio of 1:1-100 to carry out acidification or acid treatment, followed by adding 0.05-3.5% of an dispersing agent based on the weight of the montmorillonite, boiling the mixture to remove the acid, and washing to give a liquid dispersion of modified hydrogen-montmorillonite;

2) controlling the solid content of the liquid dispersion of the modified hydrogen-montmorillonite obtained from 1) at 0.5-10% and adding an sodium modification agent in an amount of not less than the cation-exchange capacity of the montmorillonite in order to subjecting the montmorillonite to sodium modification.

In the context, the montmorillonite with a purity of not less than 90% is also referred to as purified montmorillonite, or as "high purity montmorillonite" or "high quality montmorillonite" in the art, which means purified montmorillonite prepared by purification, such as those disclosed in CN200610054632.1, WO2007090355A, CN200610055117.5 and CN200680028247.8 (WO2007051427A). Purified montmorillonite with less amount of silica impurities is preferably used as starting material in the invention so that the mineral impurities other than clay silicate can be effectively prevented from entering the subsequent procedures, and thus the quality of the modified sodium-montmorillonite is improved.

The "modified sodium-montmorillonite" according to the invention means purified montmorillonite which has been subjected to sodium modification.

Herein, "cation exchange capacity" (i.e. CEC) is defined as the degree to which a montmorillonite can adsorb and exchange cations, including exchangeable salt radical and exchangeable hydrogen, in mmol/100 kg. In the present invention, the cation exchange capacity (CEC) is determined by cobaltihexamine chloride ion exchange method, i.e. using $[Co(NH_3)_6]^{3+}$ as the exchangeable cations to determined the cation exchange capacity of montmorillonite. The method is as follows: a montmorillonite sample is ground and passed through 300 mesh, then dried at 60° C. for 3 hours and kept for further use; the obtained montmorillonite sample is mixed with certain amount of 0.025 mol/L $[Co(NH_3)_6]Cl_3$ solution, and the resultant mixture is adjusted to pH 7-8 and homogenized by shaking; after the ion exchange achieves an equilibrium state, the absorbance of the mixture is measured at 474.0 nm; the corresponding concentration C after the ion exchange is calculated from the absorbance difference between the mixture after the ion exchange and that before the ion exchange (ΔA), and the cation exchange capacity of the montmorillonite is calculated by the formula CEC=300CV/W, in which V is the volume of the solution used in the ion exchange, W is the weight of the sample. Herein, $Ca^{2+}$, $Mg^{2+}$, $Na^+$, $K^+$ contents of the montmorillonite are measured by plasma emission spectrometry. The above mentioned method is not limiting.

Percentage values used in the context denote percent by weight, unless otherwise specified.

In a preferred embodiment of the present invention, the purified montmorillonite is any one selected from the group consisting of purified sodium-montmorillonite, purified sodium-calcium-montmorillonite, purified hydrogen-montmorillonite, purified magnesium-montmorillonite, natural sodium-montmorillonite and purified calcium-montmorillonite, or any combination thereof. The purity of the purified montmorillonite is not less than 93%, preferably not less than 95%, more preferably not less than 97%.

In a preferred embodiment of the present invention, the acid is any one selected from the group consisting of inorganic acids and organic acids, or any combination thereof. The inorganic acids include but are not limited to monoacid, diacid or triacid. The monoacid is selected from the group consisting of hydrochloric acid, nitric acid, hydrobromic acid and hydrofluoric acid. The diacid is selected from the group consisting of sulfuric acid and sulfonic acid. The triacid is selected from the group consisting of phosphoric acid. The inorganic acid is preferably a monoacid, and most preferably hydrochloric acid or nitric acid. The organic acids include but are not limited to hydroxyl acid, keto acid or alpha-hydroxyl acid, or any combination thereof. The organic acid is preferably any one selected from the group consisting of acetic acid, oxalic acid, citric acid, succinic acid, formic acid, propanoic acid, butyric acid, propanedioic acid, butanedioic acid, pyruvic acid, glutamic acid, tartaric acid, malic acid, lactic acid, fumaric acid, itaconic acid, ascorbic acid, fumaric acid and α-ketoglutaric acid, or any combination thereof, and more preferably any one selected from the group consisting of acetic acid, oxalic acid, citric acid, succinic acid, propanoic acid, butyric acid, butanedioic acid and propanedioic acid, or any combination thereof. The concentration of the acid may be 0.5-8 mol/L, preferably 0.8-6 mol/L, more preferably 1-5 mol/L, and most preferably 2-4 mol/L.

In some embodiments, the molar ratio of the inorganic acid to the organic acid in the acid is 5-150:5-200, preferably 10-120:10-150, more preferably 20-100:20-120, and most preferably 30-80:30-100.

In some embodiments of the present invention, the mass ratio of the montmorillonite to the acid is 1:2-50, preferably 1:2.5-25, more preferably 1:3-10.

In some embodiments of the present invention, the acidification or acid treatment in the step 1) may be carried out several times, preferably 1-10 times, more preferably 2-8 times, even more preferably 3-6 times, and most preferably 4-5 times. The acid is preferably removed by centrifuging or filtration.

The "dispersing agent" as used in the invention is also referred to as "ore-dressing agent", "high purity agent" or "high purity treatment agent" in the art.

In some embodiments of the present invention, the dispersing agent is any one selected from the group consisting of sodium hexametaphosphate, sodium trimetaphosphate, sodium dimetaphosphate, sodium polyacrylate, aqueous ammonia, sodium pyrophosphate, sodium polyphosphate, acrylic acid, sodium acrylate, sodium silicate, trisodium phosphate, sodium hydroxide, sodium carbonate, sodium bicarbonate, sodium carboxymethyl cellulose, sodium citrate, $Na_2HPO_4$, $NaH_2PO_4$, NaCl, NaF, sodium sulfate, silica sol, urea, polysorbate, hydrochloric acid, acetic acid and oxalic acid, or any combination thereof, preferably any one selected from the group consisting of sodium hexametaphosphate, sodium pyrophosphate, sodium polyphosphate, sodium trimetaphosphate, sodium dimetaphosphate, sodium polyacrylate, trisodium phosphate, sodium citrate, $Na_2HPO_4$, NaCl, NaF, urea, $NaH_2PO_4$, aqueous ammonia, sodium sulfate, hydrochloric acid, acetic acid and oxalic acid, or any combination thereof.

In a preferred embodiment of the present invention, the amount of the dispersing agent used is 0.05-3.0%, preferably 0.15-2.5%, more preferably 0.25-2.0%, and most preferably 0.35-1.5%, based on the amount of the purified montmorillonite used.

In some embodiments of the present invention, the duration for boiling in the step 1) is 0.5-100 hours, preferably 2-70 hours, more preferably 3-40 hours, and most preferably 5-20 hours.

In some embodiments of the present invention, the temperature for boiling in the step 1) is 30-100° C., preferably 40-95° C., more preferably 50-90° C., further more preferably 60-85, and most preferably 70-80° C.

In some embodiments of the present invention, the solid content of the liquid dispersion of the modified hydrogen-montmorillonite in the step 2) is 1-9%, preferably 2-8%, more preferably 3-6%, and most preferably 4-5%.

In a preferred embodiment of the present invention, the sodium modification agent is a soluble sodium salt conventionally used in the art, which is any one selected from the group consisting of sodium hexametaphosphate, sodium trimetaphosphate, sodium dimetaphosphate, sodium polyacrylate, sodium pyrophosphate, sodium polyphosphate, sodium acrylate, sodium silicate, sodium phosphate, sodium hydroxide, sodium carbonate, sodium bicarbonate, sodium carboxymethyl cellulose, $Na_2HPO_4$, $NaH_2PO_4$, NaCl, NaF, sodium sulfate and sodium citrate, or any combination thereof, preferably any one selected from the group consisting of sodium hexametaphosphate, sodium pyrophosphate, sodium polyphosphate, sodium trimetaphosphate, sodium dimetaphosphate, sodium phosphate, sodium citrate, $Na_2HPO_4$, $NaH_2PO_4$, NaCl, NaF, sodium sulfate, sodium hydroxide, sodium carbonate and sodium bicarbonate, or any combination thereof.

In a preferred embodiment of the present invention, the amount of the sodium modification agent used is slightly in excess of the cation exchange capacity of the montmorillonite, for example, by 0.5-10%, preferably by 1-8%, more preferably by 2-6%, and most preferably by 3-5%.

In some embodiments of the present invention, the amount of the sodium modification agent used is 1-20%, preferably 2-15%, more preferably 3-10%, and most preferably 4-7.5%, based on the amount of the modified hydrogen-montmorillonite used.

In some embodiments of the present invention, the solid content of the sodium modification slurry is 1-8%, preferably 1.5-6%, and more preferably 2-5%.

Conventional solid-liquid centrifugal separation equipments (for example three-column centrifuge or tubular centrifuge) have difficulty in achieving complete solid-liquid separation due to the high viscosity of the montmorillonite slurry, and in fulfilling the requirement of large scale production due to their high cost, low safety, short working life and low productive efficiency. In a preferred embodiment of the present invention, the montmorillonite slurry is washed or concentrated by membrane filtration technique or centrifugal separation washing technology, preferably by membrane filtration technique. Membrane filtration technique (also referred as "dialysis membrane cleaning") will not only significantly improve the efficiency of montmorillonite production, but also have the advantages such as low equipment investment, low energy consumption, and high purity and yield of product, being suitable for large scale production. In addition, membrane filtration technique, in which the waste water produced from washing can be recycled after being treated by reverse osmosis membrane, is an environment-friendly separation technology In a preferred embodiment of the present invention, the membrane filtration is carried out in a dialysis membrane equipment by stirring the washed or concentrated slurry mechanically or with the effect of compressed air and then feeding it to the dialysis membrane by means of circulation pump or air pressure to remove the filtrate smaller than the pore size of the filter membrane by pressure difference.

In a preferred embodiment of the present invention, the dialysis membrane is ceramic membrane, which is made of any material selected from the group consisting of zirconium oxide and aluminum oxide, or any combination thereof.

In a preferred embodiment of the present invention, the pore size of the dialysis membrane is 20 nm-200 nm, preferably 50 nm-150 nm.

In a preferred embodiment of the present invention, the dialysis membrane is applicable in the pH range of 0-14.

In a preferred embodiment of the present invention, the dialysis membrane may be regenerated by physical washing, chemical washing or physicochemical washing under high fluid speed and low pressure. Physical washing means washing the dialysis membrane by, for example, high speed water flow, mechanism or any combination thereof to remove pollutants. Chemical washing means washing the dialysis membrane with, for example, chemical agents which do not destroy the membrane material but can dissolve or replace pollutants. For example, inorganic strong acids for converting insoluble pollutants to soluble substance, organic acids for removing mineral salt precipitates, chelating agents for complexing inorganic ions in pollutants, or surfactants for removing organic pollutant, may be used to reduce the salts deposited on the membrane surface and in the pores, thereby reducing or removing pollutant adsorbed on the membrane surface and in the pores, and recovering the membrane flux.

In a preferred embodiment of the present invention, severely polluted dialysis membrane is cleaned by washing alternatively with strong acids and strong base and, if appropriate, additional oxidants (for example, sodium hypochlorite) and surfactants, or under high fluid speed and low pressure further by means of back flushing and water rinsing, in order to recover membrane flux.

In a further preferred embodiment of the present invention, the concentrated sodium modification slurry is dried and ground.

The preparation process according to the invention therefore has the advantages such as high yield of product, low cost of production and easy industrialized.

The invention also provides a modified sodium-montmorillonite prepared by the above-mentioned method.

In order to further improve the physical and chemical properties of the modified sodium-montmorillonite according to the invention, the above obtained modified sodium-montmorillonite may be further subjected to high-speed shearing, high-pressure homogenizing, air flow pulverizing and so on, to give a modified nanometered sodium-montmorillonite.

The invention also provides a modified nanometered sodium-montmorillonite, characterized in that the $Na^+$ content (calculated as $Na_2O$) in the modified nanometered sodium-montmorillonite is not less than 2%, preferably not less than 3%, more preferably not less than 4%, and most preferably not less than 5%.

In some embodiments of the present invention, the $Ca^{2+}$ content (calculated as CaO) in the modified nanometered sodium-montmorillonite is not more than 1%, preferably not more than 0.5%, more preferably not more than 0.1%, and most preferably not more than 0.05%.

In some embodiments of the present invention, the d-value corresponding to $d_{002}$ peak in the X-ray powder diffraction spectrum of the modified nanometered sodium-montmorillonite is 5.50 Å-7.00 Å, preferably 5.75 Å-6.75 Å, more preferably 6.00 Å-6.5 Å, and most preferably 6.25 Å.

In some embodiments of the present invention, the particle size of the modified nanometered sodium-montmorillonite is not more than 1 µm, preferably not more than 0.8 µm, more preferably not more than 0.6 µm, further more preferably not more than 0.4 µm, and most preferably not more than 0.2 µm.

In some embodiments of the present invention, the cation exchange capacity (CEC) of the modified nanometered sodium-montmorillonite is 90-150 mmol/100 g, preferably 100-145 mmol/100 g, more preferably 110-140 mmol/100 g, and most preferably 115-135 mmol/100 g.

In some embodiments of the present invention, the swelling capacity of the modified nanometered sodium-montmorillonite is not less than 4.0, preferably not less than 5.0, more preferably not less than 7.0, further more preferably not less than 9.0, even more preferably not less than 10.0, and most preferably not less than 12.0.

In some embodiments of the present invention, the adsorption of strychnine sulfate by per gram of the modified nanometered sodium-montmorillonite according to the invention is 0.30-0.70 g, preferably 0.40-0.65 g, and more preferably 0.5-0.6 g.

In some embodiments of the present invention, the content of heavy metal in the modified nanometered sodium-montmorillonite is not more than 10 ppm, preferably not more than 7 ppm, more preferably not more than 5 ppm, and most preferably not more than 3 ppm-4 ppm.

In some embodiments of the present invention, the impurity level in the modified nanometered sodium-montmorillonite is not more than 5%, preferably not more than 4%, more preferably not more than 3%, further more preferably not more than 2%, even more preferably not more than 1%, and most preferably not more than 0.5%.

In some embodiments of the present invention, the thixotropic index of the modified nanometered sodium-montmorillonite is not less than 1, preferably not less than 2, more preferably not less than 3, and most preferably not less than 4.

The present invention also provides a method for preparing a modified nanometered sodium-montmorillonite, comprising the following steps: preparing an aqueous solution of the modified sodium-montmorillonite according to the present invention, which has a purity of not less than 95%, with a solid content of 0.5-60%; dispersing and homogenizing the aqueous solution by high-speed shearing effect in, for example, high-speed shearing machine, high-speed dispersor, ball mill or high pressure homogenizer; drying; and pulverizing.

In a preferred embodiment of the present invention, the purity of the modified sodium-montmorillonite is not less than 96%, preferably not less than 97%, more preferably not less than 98%, and most preferably not less than 99%.

In a preferred embodiment of the present invention, the concentration of the aqueous solution is 5-50%, preferably 10-40%, more preferably 15-30%, and most preferably 20-25%.

In a preferred embodiment of the present invention, the homogenization pressure is not less than 10 MPa, preferably 20-800 MPa, more preferably 30-600 MPa, further more preferably 50-500 MPa, and most preferably 80-300 MPa.

In a preferred embodiment of the present invention, the high pressure homogenizer is any one selected from group consisting of middle-high pressure homogenizer, super-high pressure homogenizer, nanometer super-high pressure homogenizer, nanometer ram machine and high pressure micro jet homogenizer, or any combination thereof.

In a preferred embodiment of the present invention, pulverization is carried out by air flow pulverizing after coarse grinding.

In a preferred embodiment of the present invention, the fineness of the pulverized particles is not less than 300 meshes, preferably not less than 500 meshes, further preferably not less than 1000 meshes, more preferably not less than 3000 meshes, and most preferably not less than 5000 meshes.

In an exemplary embodiment, the solid particles of the modified sodium-montmorillonite according to the invention are pre-dispersed in water medium by strong shearing of a high-speed disperser and then subjected to high pressure homogenization (also referred to as "delamination") in continuous or multiple-stage mode from low pressure to high pressure to give particles with an average diameter of not more than 1 µm. By such forced pulverizing, the following effects can be achieved, i.e. increased edges of the particles, improved hydration delaminating performance, increased number of "carriages", improved adsorption performance, thixotropy and gelling property, and thus enhanced efficacy.

The invention also provides a modified nanometered sodium-montmorillonite prepared by the above-mentioned method.

"Modified nanometered sodium-montmorillonite" according to the invention is also referred to as "nanometered modified sodium-montmorillonite".

The invention also provides a pharmaceutical composition used for treating digestive tract diseases, composed of the modified sodium-montmorillonite or the modified nanometered sodium-montmorillonite according to the invention and pharmaceutically acceptable carriers.

In a preferred embodiment of the present invention, the digestive tract diseases are selected from the group consisting of digestive tract ulcer, diarrhea or gastritis, the gastritis preferably being chronic gastritis, more preferably being chronic atrophic gastritis.

In a preferred embodiment of the present invention, the purity of the modified sodium-montmorillonite or the modified nanometered sodium-montmorillonite in the composition is not less than 95%, preferably not less than 96%, more preferably not less than 97%, further more preferably not less than 98%, even more preferably not less than 99%, and most preferably not less than 99.5%.

In a preferred embodiment of the present invention, the weight ratio (on dry basis) of the modified sodium-montmorillonite or the modified nanometered sodium-montmorillonite to auxiliaries in the composition is (0.001-99):(1-99), preferably (0.001-90):(1-95), more preferably (0.001-80):(1-90), and most preferably (0.001-70):(1-85).

In a preferred embodiment of the present invention, the content of the modified sodium-montmorillonite or the modified nanometered sodium-montmorillonite in the composition by weight is 1-99%, preferably 5-95%, more preferably 10-90%, further more preferably 15-85%, and most preferably 20-80%.

In a preferred embodiment of the present invention, the cation exchange capacity (CEC) of the modified sodium-montmorillonite or the modified nanometered sodium-montmorillonite is 90-150 mmol/100 g, preferably 100-145 mmol/100 g, more preferably 110-140 mmol/100 g, and most preferably 115-135 mmol/100 g.

In a preferred embodiment of the present invention, the swelling capacity of the modified sodium-montmorillonite or the modified nanometered sodium-montmorillonite is not less than 4.0, preferably not less than 5.0, more preferably not less than 7.0, further more preferably not less than 9.0, even more preferably not less than 10.0, and most preferably not less than 12.0.

In a preferred embodiment of the present invention, the adsorption of strychnine sulfate by per gram of the modified sodium-montmorillonite or the modified nanometered sodium-montmorillonite in the composition is 0.30-0.70 g, preferably 0.40-0.65 g, and more preferably 0.5-0.6 g.

In a preferred embodiment of the present invention, the content of heavy metal in the modified sodium-montmorillonite or the modified nanometered sodium-montmorillonite in the composition is not more than 10 ppm, preferably not more than 7 ppm, more preferably not more than 5 ppm, and most preferably not more than 3 ppm-4 ppm.

In a preferred embodiment of the present invention, the impurity level in the modified sodium-montmorillonite or the modified nanometered sodium-montmorillonite in the composition is not more than 5%, preferably not more than 4%, more preferably not more than 3%, further more preferably not more than 2%, even more preferably not more than 1%, and most preferably not more than 0.5%.

In a preferred embodiment of the present invention, the $Ca^{2+}$ content (calculated as CaO) in the modified sodium-montmorillonite or the modified nanometered sodium-montmorillonite is not more than 1%, preferably not more than 0.5%, more preferably not more than 0.1%, and most preferably not more than 0.05%.

In a preferred embodiment of the present invention, the $Na^+$ content (calculated as $Na_2O$) in the modified sodium-montmorillonite or the modified nanometered sodium-montmorillonite is not less than 2%, preferably not less than 3%, more preferably not less than 4%, and most preferably not less than 5%.

In a preferred embodiment of the present invention, the thixotropic index of the modified sodium-montmorillonite or the modified nanometered sodium-montmorillonite is not less than 1, preferably not less than 2, more preferably not less than 3, and most preferably not less than 4.

In a preferred embodiment of the present invention, the d-value corresponding to $d_{002}$ peak in the X-ray powder diffraction spectrum of the modified sodium-montmorillonite is 5.50 Å-7.00 Å, preferably 5.75 Å-6.75 Å, more preferably 6.00 Å-6.5 Å, and most preferably 6.25 Å.

The composition according to the invention may be in various types of formulations well known in the art, which are prepared by conventional formulating technology in the art. Formulations suitable for the present invention are oral formulations or topical formulations, preferably oral formulations.

The oral formulations are selected from tablets, suspensions, capsules, granules, pills, powders, drop pills, syrups, mixtures, distillates, effervescent agents, pastes, emulsions, medicinal teas and so on; preferably being powders, suspensions, granules, tablets, capsules or effervescent agents.

The topical formulations suitable for the present invention are selected from gels, emplastrums, strappings, creams, ointments, liniments, lotions, suppositories, smearing preparations, pastes, plasters and so on, preferably being gels.

The pharmaceutically acceptable carriers comprise customary excipients or auxiliaries well known in the art for preparing the above-mentioned formulations, which comprise, but are not limited to, fillers (also referred as diluents), lubricants (also referred as flow aids or antitackiness agent), dispersing agents, wetting agents, adhesives, regulators, solubilizers, antioxidants, bacteriostats, emulsifiers, flavoring agents, perfumes and the like. Adhesives may be, for example, syrups, arabic gum, gelatin, sorbitol, tragacanth gum, cellulose and derivatives thereof, gelatin size, syrup, starch paste or polyvinylpyrrolidone, preferable cellulose derivatives being microcrystalline cellulose, sodium carboxymethyl cellulose, ethyl cellulose or hydroxylpropylmethyl cellulose. Fillers may be, for example, lactose, powdered sugar, dextrin, starch and derivatives thereof, cellulose and derivatives thereof, inorganic calcium salt, sorbitol or glycine, preferable inorganic calcium salt being calcium sulfate, calcium phosphate, calcium hydrogen phosphate or precipitated calcium carbonate. Lubricants may be, for example, ultra-fine silica gel, magnesium stearate, talc powder, aluminium hydroxide, boric acid, hydrogenated vegetable oil or polyethylene glycol. Disintegrating agents may be, for example, starch and derivatives thereof, polyvinylpyrrolidone, cross-linked polyvinylpyrrolidone or microcrystalline cellulose, preferable starch derivatives being sodium carboxymethyl starch, sodium starch glycollate, pregelatinized starch, modified starch, hydroxylpropyl starch or corn starch. Wetting agents may be, for example, sodium dodecylsulfate, water or alcohol, and the like.

In addition, active ingredients can be mixed with pharmaceutically acceptable sustained-release or controlled-release carriers as per the preparation requirements, and then prepared as pellets, such as sustained-release pellets or controlled-release pellets, for example, by coating with retardant or microencapsulation according to the known methods for preparing sustained-release or controlled-release formulations. The sustained-release or controlled-release carriers comprise, but are not limited to, grease admixtures, hydrophilic colloids, coating retardant and so on. The grease admixture is any one selected from the group consisting of glycerol monostearate, hydrogenated castor oil, mineral oil, polysiloxane and dimethyl siloxane, or any combination thereof. The hydrophilic colloid is any one selected from the group consisting of sodium carboxymethyl cellulose, hydroxylpropyl cellulose, hydroxylpropyl methyl cellulose, PVP, arabic gum, tragacanth gum and carbopol, or any combination thereof. The coating retardant is any one selected from the group consisting of ethyl cellulose (EC), hydroxylpropyl methyl cellulose (HMPC), polyvinylpyrrolidone (PVP), cellulose acetate phthalate (CAP) and acrylic resin, or any combination thereof.

As to the modified sodium-montmorillonite, the modified nanometered sodium-montmorillonite or the pharmaceutical composition thereof according to the invention, technical features of different preference grades in the above-mentioned embodiments can be optionally combined with each other.

The invention also relates to the use of the modified sodium-montmorillonite or the modified nanometered sodium-montmorillonite or the pharmaceutical composition thereof in the manufacture of medicaments having the following therapeutical applications.

In a preferred embodiment of the present invention, the medical use of the modified sodium-montmorillonite or the modified nanometered sodium-montmorillonite is selected from the following: (1) use of the modified sodium-montmorillonite or the modified nanometered sodium-montmorillonite in the manufacture of medicaments for treating digestive tract diseases, which include but are not limited to acute or chronic diarrhea, reflux esophagitis, acute or chronic gastritis, peptic ulcer, irritable bowel syndrome, inflammatory bowel disease, gastritis and the like, preferably the gastritis being chronic gastritis, more preferably chronic atrophic gastritis, and most preferably said medicaments having reversibly therapeutic effect on chronic atrophic gastritis; (2) use of the modified sodium-montmorillonite or the modified nanometered sodium-montmorillonite in the manufacture of medicaments for preventing hyperthyroidism; (3) use of the modified sodium-montmorillonite or the modified nanometered sodium-montmorillonite in the manufacture of medicaments for treating chronic renal failure; (4) use of the modified sodium-montmorillonite or the modified nanometered sodium-montmorillonite in the manufacture of medicaments for preventing and/or treating halitosis; (5) use of the modified sodium-montmorillonite or the modified nanometered sodium-montmorillonite in the manufacture of medicinal carriers or medicinal auxiliaries, for example, the use of the modified sodium-montmorillonite as medicinal carrier or medicinal auxiliary to be combined with certain antibiotics or enzymes to form a complex medicament, such as streptomycin-montmorillonite complex, preferably as the matrix of oral formulations, topical formulations, sustained release formulations or controlled release formulations, more preferably as the matrix of tablets, suspensions, capsules, granules, pills, powders, drop pills, syrups, mixtures, distillates, effervescent agents, pastes, medicinal teas, bioadhesive preparations, gels, ointments, creams, suppositories, emulsions, pastes, inorganic antiseptics, transdermal preparations, liniments, lotions, smearing preparations, plasters, cosmetics or suspensions, the medicament being any one selected from the group consisting of oral formulations, topical formulations, sustained release formulations and controlled release formulations, or any combination thereof; (6) use of the modified sodium-montmorillonite or the modified nanometered sodium-montmorillonite in the manufacture of medicaments for treating dermatosis; (7) use of the modified sodium-montmorillonite or the modified nanometered sodium-montmorillonite in the manufacture of medicaments for alleviating drunkness and protecting liver to prevent ethanol-induced liver injury; (8) use of the modified sodium-montmorillonite or the modified nanometered sodium-montmorillonite in the manufacture of medicaments having an effect of eliminating or killing *Helicobacter pylori* for controlling gastrointestinal tract diseases resulted from infection by *Helicobacter pylori*, such gastric ulcer, duodenal ulcer and the like.

In a preferred embodiment of the present invention, the daily dosage of the modified sodium-montmorillonite or the modified nanometered sodium-montmorillonite according to the invention is 0.5-10 g, preferably 1-8 g, more preferably 1.5-6 g, further more preferably 2-4 g, and most preferably 2-3 g. The exact daily dosage of the modified sodium-montmorillonite or the modified nanometered sodium-montmorillonite may be adjusted properly according to factors such as the patient's disease, physical fitness, body weight, age, sex and the like.

The modified sodium-montmorillonite or the modified nanometered sodium-montmorillonite according to the invention is superior to natural montmorillonite in terms of CEC, adsorption and expansibility. Moreover, it features much longer adhesion time with soft tissue (for example, mucous membrane between stomach and intestine, mucous membrane between skin layers, oral mucosa), longer residence time of active ingredients in soft tissue, longer exchanging time and higher exchanging frequency of active ingredients with the body, and targeted administration and controlled release of active ingredients, which can enhance the bioavailability and drug safety of the active ingredients. Consequently, the modified sodium-montmorillonite or the modified nanometered sodium-montmorillonite according to the invention can be used in the manufacture of medicinal or food auxiliaries as described hereinbelow:

1) As a carrier of a bioadhesive preparation for controlling drug release and reducing stimulation of surface-active substances to skin. The bioadhesive preparation is selected from the group consisting of buccal bioadhesive preparation, nasal bioadhesive preparation, ophthalmic bioadhesive preparation, vaginal bioadhesive preparation, rectal bioadhesive preparation, gastrointestinal bioadhesive preparation and the like. For example, the modified sodium-montmorillonite according to the invention used in a vaginal mucosa adhesive drug delivery system (AmDDS) of nonoxynol can enhance the interaction of drug and mucin polymer of vaginal mucosa and elongate the duration of drug release. The modified sodium-montmorillonite according to the invention, when formulated in a gastric bioadhesive with bismuth potassium citrate, can not only extend the residence time of bismuth potassium citrate in gastrointestinal tract, but also show synergetic effects in eliminating or killing *Helicobacter pylori*, greatly reduce the sudden release of bismuth and thus enhance the drug safety. When formulated in a gastrointestinal tract (colon) targeted release preparation along with antitumor drugs (anti-colon cancer drugs), the modified sodium-montmorillonite according to the invention can extend the effective time in the gastrointestinal tract, control the releasing rate, improve the bioavailability and drug safety, and reduce the adverse effects of the antitumor drugs.

2) As a carrier of a gel. An aqueous solution of the modified sodium-montmorillonite with a concentration in a certain range may be used as a good matrix of gel since it has the properties of water dispersible matrix and good adhesion, film forming ability and bacteria exclusive adsorption without oily feeling and stimulus to skin and mucosa. It can be readily coated and adhere to skin, and can absorb and remove tissue exudates. Thus, it can be used as superior pharmaceutically acceptable carrier of electrocardiogram diagnosis gel, ultrasonic diagnosis gel, dental gel, dentinogenic cement, tooth powder for treating oral disease, thickener for toothpaste or transdermal gel.

3) As a matrix of semi-solid formulations such as water-soluble ointment, cream, suppository and the like due to the suspending ability, adhesion and ability of improving rheology of the modified sodium-montmorillonite or the modified nanometered sodium-montmorillonite. For example, a suppository prepared from the modified sodium-montmorillonite or the modified nanometered sodium-montmorillonite combined with suitable amount of guaiac gum, CMC, agar, PVP, oleic acid, glycerol, propylene glycol and distilled water has properties of being difficult to deform or liquefy at normal temperature, thus in favor of diffusion and absorption of drugs.

4) As a matrix of medicinal paste, inorganic antiseptic, transdermal ointment or emulsion. For example, the modified sodium-montmorillonite or the modified nanometered sodium-montmorillonite with MgO incorporated in has good hydrophilicity and dispersibility, resulting in an inorganic antiseptic having good effect on *Bacillus aeruginosus*.

5) As a suspending agent. It has substantively better suspending effect than sodium hydroxymethyl cellulose, sodium carboxymethyl starch and sodium alginate.

6) As a matrix of cosmetic such as face mask, face powder, makeup, sun screen cosmetic and the like.

The invention also provides a new bioadhesive preparation of bismuth potassium citrate, composed of bismuth potassium citrate, the modified sodium-montmorillonite and/or the modified nanometered sodium-montmorillonite and other pharmaceutical auxiliaries.

In a preferred embodiment of the present invention, the content by weight percent of each ingredient in the preparation is as follows: bismuth potassium citrate is 1-98%; the modified sodium-montmorillonite and/or the modified nanometered sodium-montmorillonite is 1-98%; and the remainder is other pharmaceutical auxiliaries.

In a preferred embodiment of the present invention, the content by weight percent of each ingredient in the preparation is as follows: bismuth potassium citrate is 5-90%; the modified sodium-montmorillonite and/or the modified nanometered sodium-montmorillonite is 5-90%; and the remainder is other pharmaceutical auxiliaries.

In a preferred embodiment of the present invention, the content by weight percent of each ingredient in the preparation is as follows: bismuth potassium citrate is 7.5-85%; the modified sodium-montmorillonite and/or the modified nanometered sodium-montmorillonite is 7.5-85%; and the remainder is other pharmaceutical auxiliaries.

In addition, each dose of the preparation according to the invention contains 50-2500 mg of bismuth potassium citrate and 10-2500 mg of the modified sodium-montmorillonite and/or the modified nanometered sodium-montmorillonite, preferably 100-2000 mg of bismuth potassium citrate and 50-2000 mg of the modified sodium-montmorillonite and/or the nanometer modified sodium-montmorillonite, more preferably 150-1500 mg of bismuth potassium citrate and 100-1500 mg of the modified sodium-montmorillonite and/or the modified nanometered sodium-montmorillonite, and most preferably 200-1200 mg of bismuth potassium citrate and 150-1200 mg of the modified sodium-montmorillonite and/or the modified nanometered sodium-montmorillonite.

The invention also provides a cosmetic containing the modified sodium-montmorillonite, comprising 1-90% of the modified sodium-montmorillonite and/or the modified nanometered sodium-montmorillonite and the remainder of other auxiliaries, preferably 5-85% of the modified sodium-montmorillonite and/or the modified nanometered sodium-montmorillonite, more preferably 7.5-80%, and most preferably 10-75%.

The modified sodium-montmorillonite and/or the modified nanometered sodium-montmorillonite according to the invention can also be used for preparing the following constructive materials:

1) As an excellent water proof material. It has high water absorbing and swelling ability and can absorb water of 8-15 times of its volume and swell up to 10-30 times of its original volume. Moreover, it can form a viscous and relatively stable gel after hydration, which has strong water retention ability and can form a gel again by absorbing water even though it has lost moisture naturally after long-term storage. When it swells again from a dry and shrinking state by absorbing water, it can produce a swelling pressure as high as 0.15 MPa and thixotropy. It also has good water resistance, water-proof self-sealing property and long durability, and can be used in winter.

2) As an inorganic thickener of organic coating (for example, polyvinyl alcohol, polyvinyl acetate, acrylic acid, carboxymethyl cellulose, hydroxylethyl cellulose and the like). It has significant thickening effect and thus can greatly reduce the amount of cellulose thickeners and emulsion thickeners or other fillers (for example, light calcium carbonate, polyvinyl alcohol) used. Moreover, it almost has no adverse effect on washability and water resistance of coating membranes, and can advantageously prevent pigment and filler from precipitating. Thus, it can significantly reduce the production cost of coating.

3) As a material for preparing adhesive aids.

4) As an anti-settling agent for suspension. It has good suspendability, thixotropy and dispersibility in aqueous medium.

5) As a slurry for oil well drilling, a catalyst or decolorant in refining of petroleum, or a material for formulating drilling fluid on the site and so on.

In addition, the modified sodium-montmorillonite and/or the modified nanometered sodium-montmorillonite according to the invention can be used in the following field:

1) As a carrier in pesticides and fertilizers for reducing water content of fertilizers to prevent from blocking, increasing the granularity of fertilizers, or solving the problem in granulation caused by the high content of water or free acid contained in calcium perphosphate and the excess water produced by chemical reactions of starting materials in the production of complex fertilizer, in order to facilitate production, transportation, storage and application of fertilizers.

2) As a solid conditioner. It has a cation exchange capacity as high as about 120 mmol/100 g, a water absorption rate as high as above 200%, and a dry compression strength up to 6 kg/cm$^2$. Moreover, it has excellent water retention capacity and good adhesion. Thus, it can change the proportion of solid, liquid and gas in the soil and improve the hydrothermal condition and structure of the soil, in order to preserve moisture and fertility of the soil without contaminating the soil environment. In addition, it can enhance the buffer capacity of the soil and absorb harmful elements in the soil.

3) As a feed additive. It can increase appetite, facilitate digestion, regulate the balances in the body, enhance immune competent, prevent diseases and keep fit of farm animals. Moreover, it can increase the conversion rate of feedstuff and reduce cost for producing thereof. It is safe, reliable and palatable, and can substantively extend the shelf life of feedstuff.

4) As a carrier of premix. It has good flowability, low tendency of dust emission. When being processed, it does not tend to delaminate and can be readily mixed homogenously. Moreover, it has strong adsorption to various vitamins and microelements and can prevent against damp, mildew, moth, deterioration and so on.

5) As an adhesive of granulated feedstuff and aquaculture feedstuff for completely replacing conventionally used forming adhesives such as carboxyl cellulose and wheat middling. It has good adhesive effect and formability, so that the feedstuff can be formed with low cost and have regular granular shape, smooth surface and good appearance.

6) As an antidote in feedstuff for preventing acidosis caused by feeding too much fine fodder or indigestion and protecting farm animals against harm caused by toxins contained in feedstuff or mycins produced during the storage of feedstuff.

7) As a diluent of fermented feedstuff for extending the shelf life of fermented feedstuff.

8) As an impervious material for landfill. It can enhance water proof effect and impervious ability of concrete, so as to prevent harmful substance from polluting underground water.

9) As an agent for disposing nuclear waste from atomic plant, a cushion material or backfill material for highly dangerous waste for preventing and buffering the diffusion of radioactive waste, and protecting environment and human against radioactive pollutant.

10) As an air purifying preparation for adsorbing sulfur oxide and nitrogen oxide in the air to purify air.

11) As a material for preparing nanocomposites with mechanical, thermal, electrical, magnetic and optical properties different from general macrocomposites.

12) As a clarificant in the decoloring process of various oils or for wines and juices, and for decolorizing, deodorizing and impurity treatment of animal and vegetable oils.

13) As an industrial catalyst, carrier or adsorbent for solving environmental pollution problems caused by large amount of waste acid, corrosion of equipments, product separation difficulties in acid (such as $H_2SO_4$, $AlCl_3$) catalysis process.

The invention will be illustrated in more details by the following examples. The examples according to the invention are only intended to explain the technical solutions of the present invention, not to limit the subject and scope of the present invention.

Herein, the modified sodium-montmorillonite prepared according to the present invention is referred as "modified sodium-montmorillonite B", and the modified sodium-montmorillonite prepared by the methods described in CN200610055117.5 and CN200680028247.8 (WO2007051427A) is referred as "modified sodium-montmorillonite A".

Unless otherwise specified, the "modified sodium-montmorillonite according to the invention" includes the "modified sodium-montmorillonite B" as mentioned herein and/or the "modified nanometered sodium-montmorillonite" prepared therefrom.

Montmorillonites used as starting materials in the examples is shown in table 1.

TABLE 1 montmorillonite as starting materials

| Name of monmorillonite | Physical and chemical properties |
|---|---|
| Purified calcium-montmorillonite | CEC is 110 mmol/100 g, swelling capacity > 4, 2.8% CaO |
| Purified magnesium-montmorillonite | CEC is 110 mmol/100 g, swelling capacity > 4, 7.5% MgO |
| Purified sodium-calcium-montmorillonite | CEC is 110 mmol/100 g, swelling capacity > 4, 1% CaO, 1.9% $Na_2O$ |
| Natural sodium-montmorillonite | CEC is 105 mmol/100 g, swelling capacity > 4, 2.5% $Na_2O$ |

Example 1

Preparation of Modified Sodium-Montmorillonite B-1

1) 3.0 mol/L of mixed acid (composed of hydrochloric acid, oxalic acid and acetic acid in a molar ratio of 4:10:6) was added in and mixed with purified calcium-montmorillonite in a mass ratio of 1:3 (montmorillonite to acid). Then 2% (based on the weight of the purified calcium-montmorillonite) of sodium hexametaphosphate was added. After being stirred at 70° C. for a further 4 hours, a first acidified dispersion was obtained. The first acidified dispersion was placed in a membrane dialysis filtration equipment with a pore size of 50 nm, washed with deionized water to neutral and then formulated as a dispersion of crude modified hydrogen-montmorillonite with a solid content of about 5%.

2) Hydrochloric acid and acetic acid were added to the dispersion of crude modified hydrogen-montmorillonite obtained in step 1) with stirring to make the resulted mixture contain 1.8 mol/L of hydrochloric acid and 0.4 mol/L of acetic acid. After being stirred at 60° C. for 2 hours, a second acidified dispersion was obtained. The second acidified dispersion was placed in a membrane dialysis filtration equipment with a pore size of 50 nm, washed with deionized water to neutral and concentrated to give a dispersion of crude modified hydrogen-montmorillonite with a solid content of about 5%.

3) Sulfuric acid was added to the dispersion of crude modified hydrogen-montmorillonite obtained in step 2) with stirring to make the resulted mixture contain 0.9 mol/L of sulfuric acid. After being stirred at 50° C. for 2 hours, a third acidified dispersion was obtained. The third acidified dispersion was placed in a membrane dialysis filtration equipment with a pore size of 50 nm, washed with deionized water to neutral and concentrated to give a dispersion of purified modified hydrogen-montmorillonite with a solid content of about 5%.

4) Sodium hydroxide was added to the dispersion of purified modified hydrogen-montmorillonite obtained in step 3) to make the resulted mixture contain 0.35 mol/L of sodium hydroxide. After being heated to 70° C. and continuously stirred for 36 hours, the resulted mixture was placed in a membrane dialysis filtration equipment with a pore size of 50 nm and washed with deionized water to neutral to give a dispersion of modified sodium-montmorillonite. Then the dispersion of modified sodium-montmorillonite was placed in a centrifugal separation equipment for solid-liquid separation to give a filter cake, which was dried and ground to give modified sodium-montmorillonite B-1.

The performance parameters of the modified sodium-montmorillonite B-1 are as follows: 1) $Ca^{2+}$ content (calculated as CaO) is 0.04%; 2) heavy metal content <5 ppm; 3) $Na^+$ content (calculated as $Na_2O$) is 3.6%; 4) thixotropic index in simulated gastric fluid is 6.0; 5) CEC is 135 mmol/100 g. The X-ray powder diffraction spectrum thereof is shown in FIG. 1.

Example 2

Preparation of Modified Sodium-Montnorillonite B-2

Figure 8:
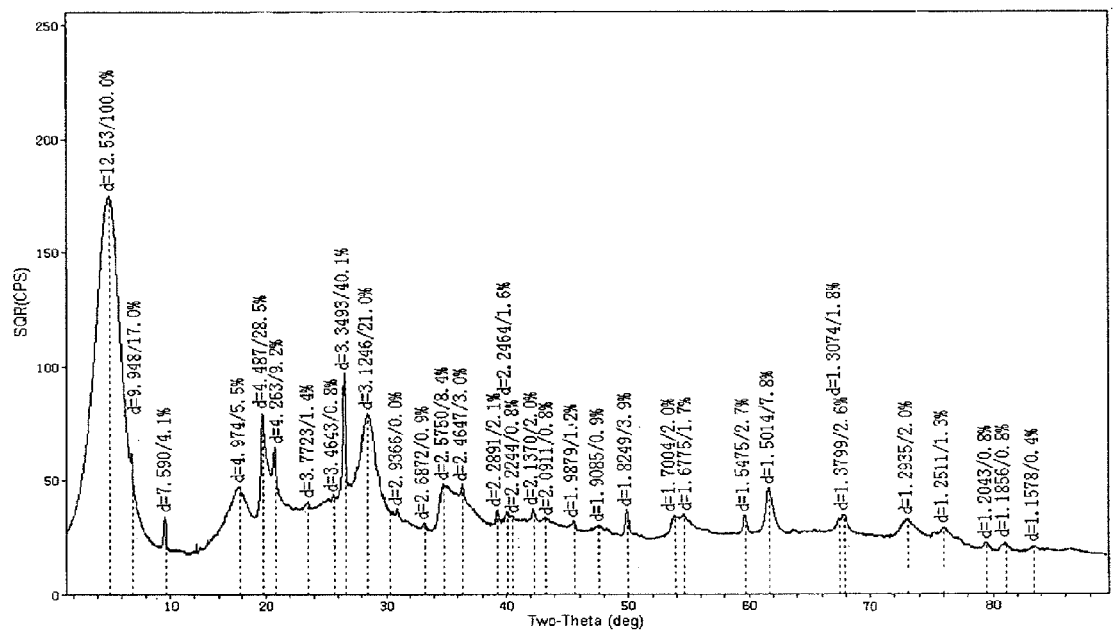
FIG. 8 is an X-ray powder diffraction spectrum of natural sodium-montmorillonite.
Figure 9:
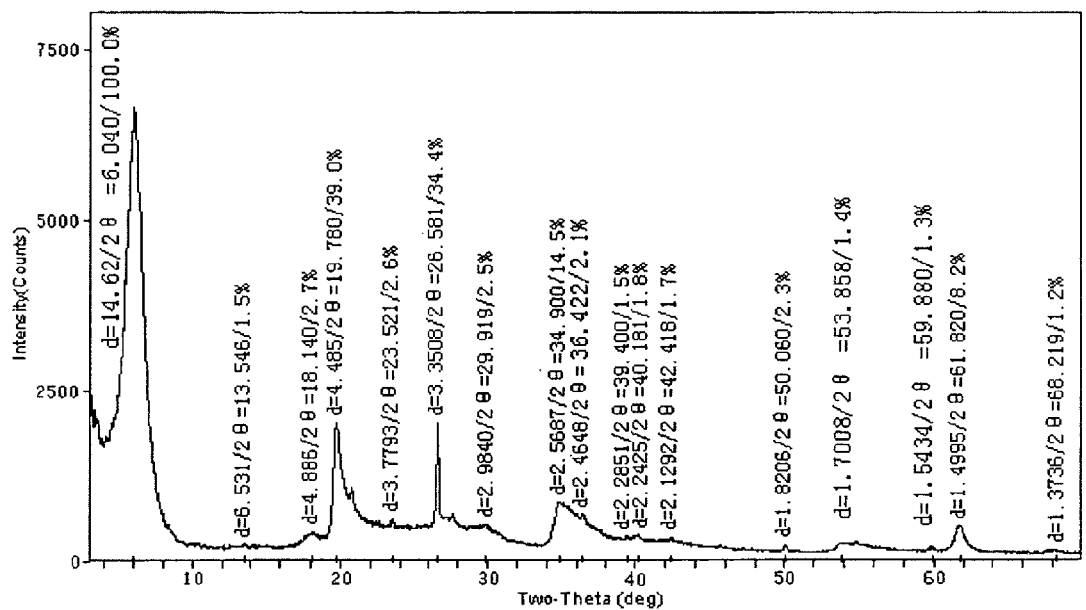
FIG. 9 is an X-ray powder diffraction spectrum of modified calcium-montmorillonite, which is prepared by the process disclosed in CN200680028247.8.
Figure 10:
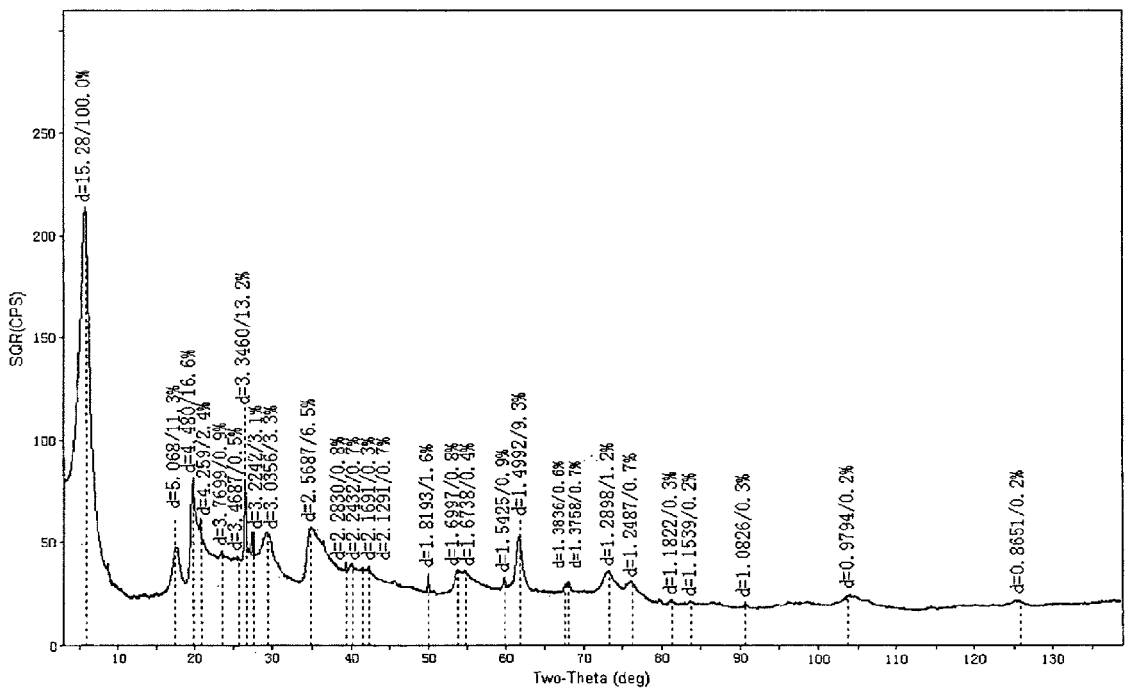
FIG. 10 is an X-ray powder diffraction spectrum of natural calcium-montmorillonite.

1) 3.5 mol/L of mixed acid (composed of sulfuric acid, oxalic acid and acetic acid in a molar ratio of 10:5:4) was added in and mixed with natural sodium-montmorillonite (its X-ray powder diffraction spectrum is shown in FIG. 8) in a mass ratio of 1:3 (montmorillonite to acid). Then 1% (based on the weight of the natural sodium-montmorillonite) of sodium hexametaphosphate was added. After being stirred at 70° C. for a further 4 hours, the mixture was press-filtered. The filter cake was washed with deionized water to neutral and then formulated as a dispersion of crude modified hydrogen-montmorillonite with a solid content of about 5%.

2) Hydrochloric acid was added to the dispersion of crude modified hydrogen-montmorillonite obtained in step 1) with stirring to make the resulted mixture contain 1.8 mol/L of hydrochloric acid. After being stirred at 60° C. for 2 hours, the mixture was press-filtered, washed with deionized water to neutral and concentrated to give a dispersion of purified modified hydrogen-montmorillonite with a solid content of about 15%.

3) Sodium carbonate was added to the dispersion of purified modified hydrogen-montmorillonite obtained in step 2) to make the resulted mixture contain 0.30 mol/L of sodium carbonate. After being heated to 70° C. and continuously stirred for 12 hours, the resulted mixture was press-filtered and washed with deionized water to neutral to give crude modified sodium-montmorillonite. Water was added to the crude modified sodium-montmorillonite to give a dispersion of crude modified sodium-montmorillonite with a concentration of 3%. The dispersion was placed in a centrifugal separation equipment for solid-liquid separation. The obtained filter cake was washed and dried at 105° C., then ground to give modified sodium-montmorillonite B-2.

Figure 2:
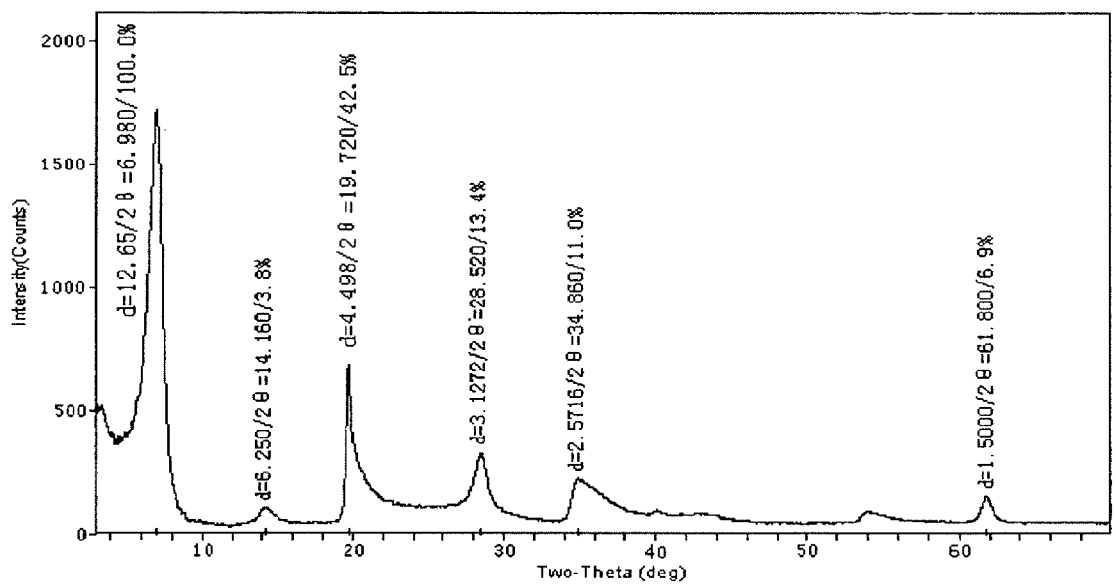
FIG. 2 is an X-ray powder diffraction spectrum of the modified sodium-montmorillonite B-2 prepared in example 2.

The performance parameters of the modified sodium-montmorillonite B-2 are as follows: 1) $Ca^{2+}$ content (calculated as CaO) is 0.1%; 2) heavy metal content <5 ppm; 3) $Na^+$ content (calculated as $Na_2O$) is 3.5%; 4) thixotropic index in simulated gastric fluid is 5.5; 5) CEC is 130 mmol/100 g. The X-ray powder diffraction spectrum thereof is shown in FIG. 2.

Example 3

Preparation of Modified Sodium-Montnorillonite B-3

1) 2.5 mol/L of nitric acid was added in and mixed with purified calcium-montmorillonite in a mass ratio of 1:3 (montmorillonite to acid). Then 1.5% (based on the weight of the purified calcium-montmorillonite) of sodium hexametaphosphate was added. After being stirred at 70° C. for a further 4 hours, a first acidified dispersion was obtained. The first acidified dispersion was centrifuged and washed with deionized water to neutral. Then water was added to give a dispersion of crude modified hydrogen-montmorillonite with a solid content of about 5%.

2) Hydrochloric acid and acetic acid were added to the dispersion of crude modified hydrogen-montmorillonite obtained in step 1) with stirring to make the resulted mixture contain 0.8 mol/L of hydrochloric acid and 0.8 mol/L of acetic acid. After being stirred at 50° C. for 2 hours, a second acidified dispersion was obtained. The second acidified dispersion was centrifuged, washed with deionized water to neutral and concentrated to give a dispersion of purified modified hydrogen-montmorillonite with a solid content of about 5%.

3) Sodium hydroxide was added to the dispersion of purified modified hydrogen-montmorillonite obtained in step 2) to make the resulted mixture contain 0.3 mol/L of sodium hydroxide. After being heated to 70° C. and continuously stirred for 40 hours, the resulted mixture was centrifuged and washed with deionized water to neutral. The obtained dispersion of modified sodium-montmorillonite was spray dried and ground to give modified sodium-montmorillonite B-3.

Figure 3:
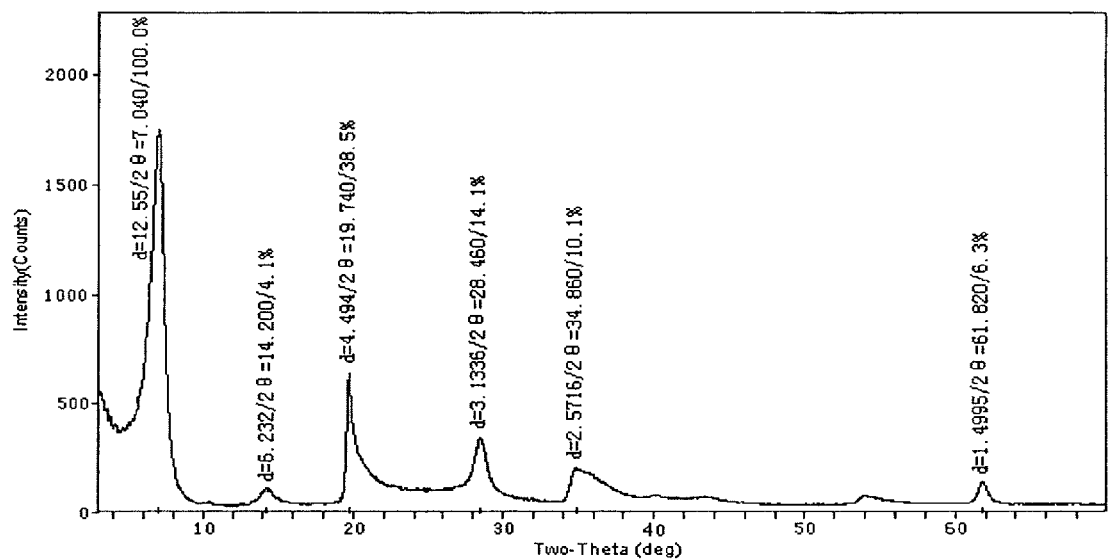
FIG. 3 is an X-ray powder diffraction spectrum of the modified sodium-montmorillonite B-3 prepared in example 3.

The performance parameters of the modified sodium-montmorillonite B-3 are as follows: 1) $Ca^{2+}$ content (calculated as CaO) is 0.21%; 2) heavy metal content <10 ppm; 3) $Na^+$ content (calculated as $Na_2O$) is 3.3%; 4) thixotropic index in simulated gastric fluid is 4.5; 5) CEC is 126 mmol/100 g. The X-ray powder diffraction spectrum thereof is shown in FIG. 3.

Example 4

Preparation of Modified Sodium-Montmorillonite B-4

1) 2.5 mol/L of mixed acid (composed of hydrochloric acid, oxalic acid and acetic acid in a molar ratio of 10:5:5) was added in and mixed with purified magnesium-montmorillonite in a mass ratio of 1:3 (montmorillonite to acid). Then 1% (based on the weight of the purified magnesium-montmorillonite) of sodium hexametaphosphate was added. After being heated to 70° C. and stirred for a further 5 hours, the mixture was centrifuged, washed with deionized water to neutral and concentrated to give a dispersion of crude modified hydrogen-montmorillonite with a solid content of about 5%.

2) Hydrochloric acid was added to the dispersion of crude modified hydrogen-montmorillonite obtained in step 1) with stirring to make the resulted mixture contain 0.8 mol/L of hydrochloric acid. After being stirred at 50° C. for 2 hours, a second acidified dispersion was obtained. The second acidified dispersion was centrifuged, washed with deionized water to neutral and concentrated to give a dispersion of purified modified hydrogen-montmorillonite with a solid content of about 5%.

3) Sodium chloride was added to the dispersion of purified modified hydrogen-montmorillonite obtained in step 2) to make the resulted dispersion contain 0.3 mol/L of sodium chloride. After being heated to 70° C. and continuously stirred for 36 hours, the resulted mixture was centrifuged and washed with deionized water to neutral. The obtained dispersion of modified sodium-montmorillonite was placed in a centrifugal separation equipment for solid-liquid separation and then concentrated to give a dispersion of modified sodium-montmorillonite with a solid content of about 50%. It was dried at 115° C. and ground to give modified sodium-montmorillonite B-4.

Figure 4:
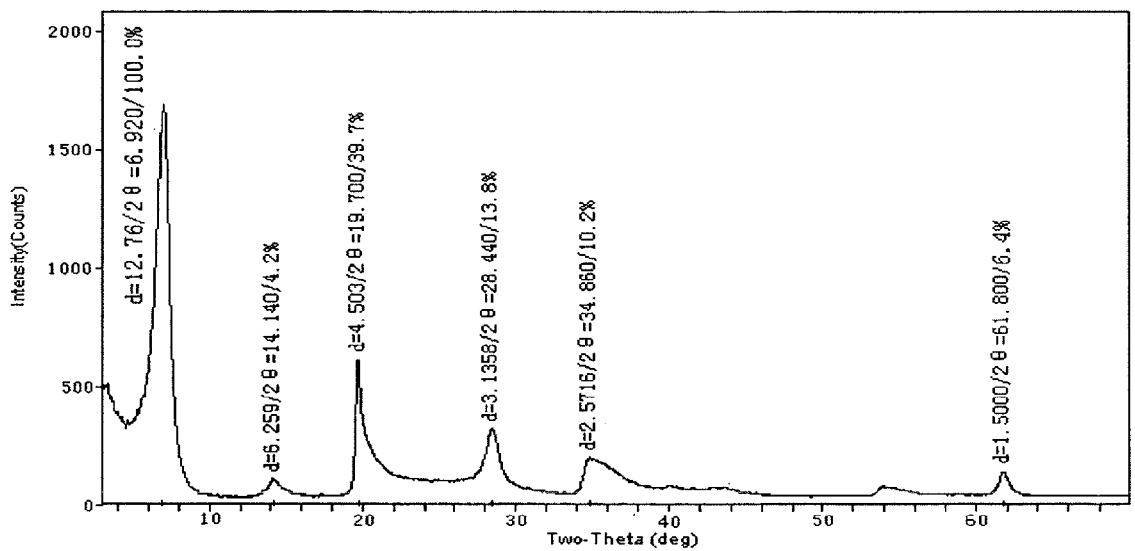
FIG. 4 is an X-ray powder diffraction spectrum of the modified sodium-montmorillonite B-4 prepared in example 4.

The performance parameters of the modified sodium-montmorillonite B-4 are as follows: 1) $Ca^{2+}$ content (calculated as CaO) is 0.3%; 2) heavy metal content <5 ppm; 3) $Na^+$ content (calculated as $Na_2O$) is 3.1%; 4) thixotropic index in simulated gastric fluid is 4.0; 5) CEC is 128 mmol/100 g. The X-ray powder diffraction spectrum thereof is shown in FIG. 4.

Example 5

Preparation of Modified Sodium-Montmorillonite B-5

1) 3.0 mol/L of mixed acid (composed of hydrochloric acid and acetic acid in a molar ratio of 10:3) was added in and mixed with purified sodium-calcium-montmorillonite in a mass ratio of 1:3 (montmorillonite to acid). Then 2% (based on the weight of the purified sodium-calcium-montmorillonite) of sodium hexametaphosphate was added. After being stirred at 70° C. for a further 4 hours, a first acidified dispersion was obtained. The first acidified dispersion was placed in a membrane dialysis filtration equipment with a pore size of 80 nm, washed with deionized water to neutral and concentrated to give a dispersion of crude modified hydrogen-montmorillonite with a solid content of about 7%.

2) Hydrochloric acid and acetic acid were added to the dispersion of crude modified hydrogen-montmorillonite obtained in step 1) with stirring to make the resulted mixture contain 0.6 mol/L of hydrochloric acid and 0.2 mol/L of acetic acid. After being stirred at 50° C. for 2 hours, a second acidified dispersion was obtained. The second acidified dispersion was placed in a membrane dialysis filtration equipment with a pore size of 50 nm, washed with deionized water to neutral and concentrated to give a dispersion of modified hydrogen-montmorillonite with a solid content of about 5%.

3) Sodium hydroxide was added to the dispersion of modified hydrogen-montmorillonite obtained in step 2) to make the resulted dispersion contain 0.2 mol/L of sodium hydroxide. After being heated to 70° C. and continuously stirred for 36 hours, the resulted mixture was placed in a membrane dialysis filtration equipment with a pore size of 50 nm and washed with deionized water to neutral. The obtained dispersion of modified sodium-montmorillonite was placed in a centrifugal separation equipment for solid-liquid separation and then concentrated to give a dispersion of modified sodium-montmorillonite with a solid content of about 6%. It was spray dried and ground to give modified sodium-montmorillonite B-5.

Figure 5:
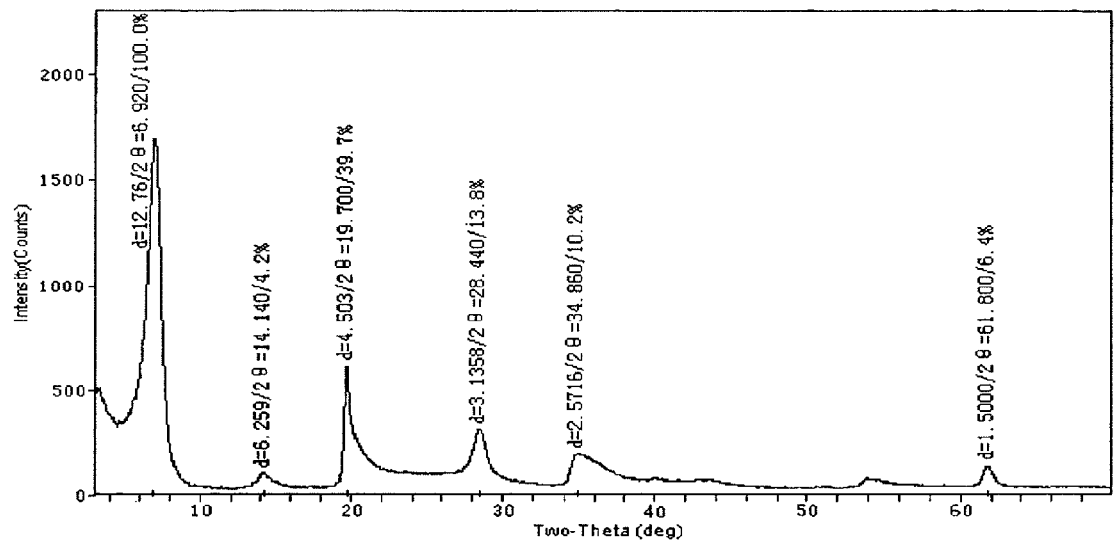
FIG. 5 is an X-ray powder diffraction spectrum of the modified sodium-montmorillonite B-5 prepared in example 5.

The performance parameters of the modified sodium-montmorillonite B-5 are as follows: 1) $Ca^{2+}$ content (calculated as CaO) is 0.4%; 2) heavy metal content <10 ppm; 3) $Na^+$ content (calculated as $Na_2O$) is 2.9%; 4) thixotropic index in simulated gastric fluid <3.5; 5) CEC is 128 mmol/100 g. The X-ray powder diffraction spectrum thereof is shown in FIG. 5.

Example 6

Preparation of Modified Sodium-Montmorillonite B-6

1) 0.6 mol/L of sulfuric acid was added in and mixed with purified calcium-montmorillonite in a mass ratio of 1:3 (montmorillonite to acid). Then 1.5% (based on the weight of the purified calcium-montmorillonite) of sodium hexametaphosphate was added. After being heated to 70° C. and stirred for a further 4 hours, a first acidified dispersion was obtained. The first acidified dispersion was placed in a high speed centrifuge for solid-liquid separation, then washed with deionized water to neutral and concentrated to give a dispersion of crude hydrogen-montmorillonite with a solid content of about 8%.

2) Sulfuric acid and acetic acid were added to the dispersion of crude hydrogen-montmorillonite obtained in step 1) with stirring to make the resulted mixture contain 0.2 mol/L of sulfuric acid and 0.3 mol/L of acetic acid. After being stirred at 50° C. for 2 hours, a second acidified dispersion was obtained. The second acidified dispersion was centrifuged, washed with deionized water to neutral and concentrated to give a dispersion of purified hydrogen-montmorillonite with a solid content of about 15%.

3) Water was added in the dispersion of purified hydrogen-montmorillonite obtained in step 2) to give a dispersion with a solid content of 6%. Sodium hydroxide was added to the dispersion to make the resulted dispersion contain 0.3 mol/L of sodium hydroxide. After being heated to 70° C. and continuously stirred for 36 hours, the resulted mixture was centrifuged and washed with deionized water to neutral to give a dispersion of modified sodium-montmorillonite with a solid content of about 2%. The dispersion was placed in a centrifugal separation equipment for solid-liquid separation. The obtained suspension was placed in a membrane dialysis filtration equipment with a pore size of 50 nm to be concentrated, giving a dispersion of modified sodium-montmorillonite with a solid content of about 4%. It was spray dried and ground to give modified sodium-montmorillonite B-6.

Figure 6:
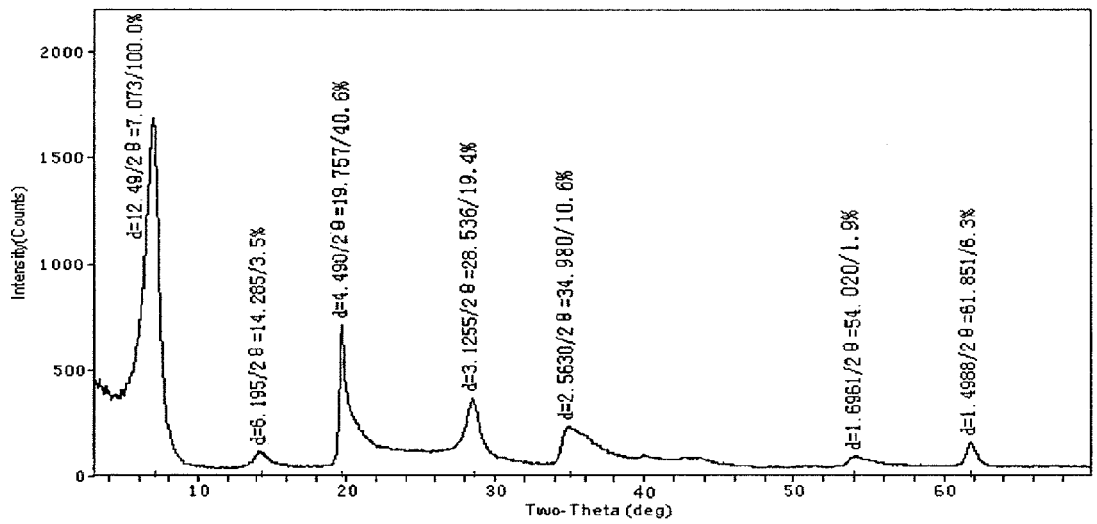
FIG. 6 is an X-ray powder diffraction spectrum of the modified sodium-montmorillonite B-6 prepared in example 6.

The performance parameters of the modified sodium-montmorillonite B-6 are as follows: 1) $Ca^{2+}$ content (calculated as CaO) is 0.5%; 2) heavy metal content <10 ppm; 3) $Na^+$ content (calculated as $Na_2O$) is 2.7%; 4) thixotropic index in simulated gastric fluid <3.5; 5) CEC is 130 mmol/100 g. The X-ray powder diffraction spectrum thereof is shown in FIG. 6.

Example 7

Preparation of Modified Montmorillonite B-7

1) 2 mol/L of hydrochloric acid was added in and mixed with purified calcium-montmorillonite in a mass ratio of 1:3 (montmorillonite to acid). Then 2% (based on the weight of the purified calcium-montmorillonite) of sodium hexametaphosphate was added. After being heated to 70° C. and stirred for a further 4 hours, a first acidified dispersion was obtained. The first acidified dispersion was placed in a membrane dialysis filtration equipment with a pore size of 50 nm, washed with deionized water to neutral, and then formulated as a dispersion of crude modified hydrogen-montmorillonite with a solid content of about 5%.

2) Hydrochloric acid was added to the dispersion of crude modified hydrogen-montmorillonite obtained in step 1) with stirring to make the resulted mixture contain 1.5 mol/L of hydrochloric acid. After being stirred at 60° C. for 2 hours, a second acidified dispersion was obtained. The second acidified dispersion was placed in a membrane dialysis filtration equipment with a pore size of 50 nm, washed with deionized water to neutral and concentrated to give a dispersion of crude modified hydrogen-montmorillonite with a solid content of about 5%.

3) Hydrochloric acid was added to the dispersion of crude modified hydrogen-montmorillonite obtained in step 2) with stirring to make the resulted mixture contain 0.8 mol/L of hydrochloric acid. After being stirred at 50° C. for 2 hours, a third acidified dispersion was obtained. The third acidified dispersion was placed in a membrane dialysis filtration equipment with a pore size of 50 nm, washed with deionized water to neutral and concentrated to give a dispersion of purified modified hydrogen-montmorillonite with a solid content of about 5%.

4) Acetic acid was added to the dispersion obtained in step 3) with stirring to make the resulted mixture contain 0.5 mol/L of acetic acid. After being stirred at 50° C. for 2 hours, a fourth acidified dispersion was obtained. The fourth acidified dispersion was placed in a membrane dialysis filtration equipment with a pore size of 50 nm, washed with deionized water to neutral and concentrated to give a dispersion of purified modified hydrogen-montmorillonite with a solid content of about 5%.

5) Acetic acid was added to the dispersion obtained in step 4) with stirring to make the resulted mixture contain 0.4 mol/L of acetic acid. After being stirred at 50° C. for 2 hours, a fifth acidified dispersion was obtained. The fifth acidified dispersion was placed in a membrane dialysis filtration equipment with a pore size of 50 nm, washed with deionized water to neutral and concentrated to give a dispersion of purified modified hydrogen-montmorillonite with a solid content of about 5%.

6) Acetic acid was added to the dispersion obtained in step 5) with stirring to make the resulted mixture contain 0.3 mol/L of acetic acid. After being stirred at 50° C. for 2 hours, a sixth acidified dispersion was obtained. The sixth acidified dispersion was placed in a membrane dialysis filtration equipment with a pore size of 50 nm, washed with deionized water to neutral and concentrated to give a dispersion of purified modified hydrogen-montmorillonite with a solid content of about 5%.

7) Sodium hydroxide was added to the dispersion of purified modified hydrogen-montmorillonite obtained in step 6) to make the resulted dispersion contain 0.5 mol/L of sodium hydroxide. After being heated to 70° C. and continuously stirred for 36 hours, the resulted mixture was placed in a membrane dialysis filtration equipment with a pore size of 50 nm and washed with deionized water to neutral. The obtained dispersion of modified sodium-montmorillonite was placed in a centrifugal separation equipment for solid-liquid separation. The obtained filter cake was dried and ground to give modified montmorillonite B-7.

The performance parameters of the modified sodium-montmorillonite B-7 are as follows: 1) $Ca^{2+}$ content (calculated as CaO) is 0.05%; 2) heavy metal content <5 ppm; 3) $Na^+$ content (calculated as $Na_2O$) is 3.65%; 4) thixotropic index in simulated gastric fluid is 5.6; 5) CEC is 125 mmol/100 g.

Example 8

Preparation of Modified Sodium-Montmorillonite A 2 mol/L of mixed acid (composed of hydrochloric acid, oxalic acid and acetic acid in a molar ratio of 4:10:6) was added in and mixed with purified calcium-montmorillonite in a mass ratio of 1:3 (montmorillonite to acid). The mixture was boiled at 100° C. for 5-6 hours and then filtered to remove the mixed acid. The filter cake was washed with deionized water to pH≥4, then dried at 100° C. and ground to 300-500 meshes to give modified hydrogen-montmorillonite.

Figure 7:
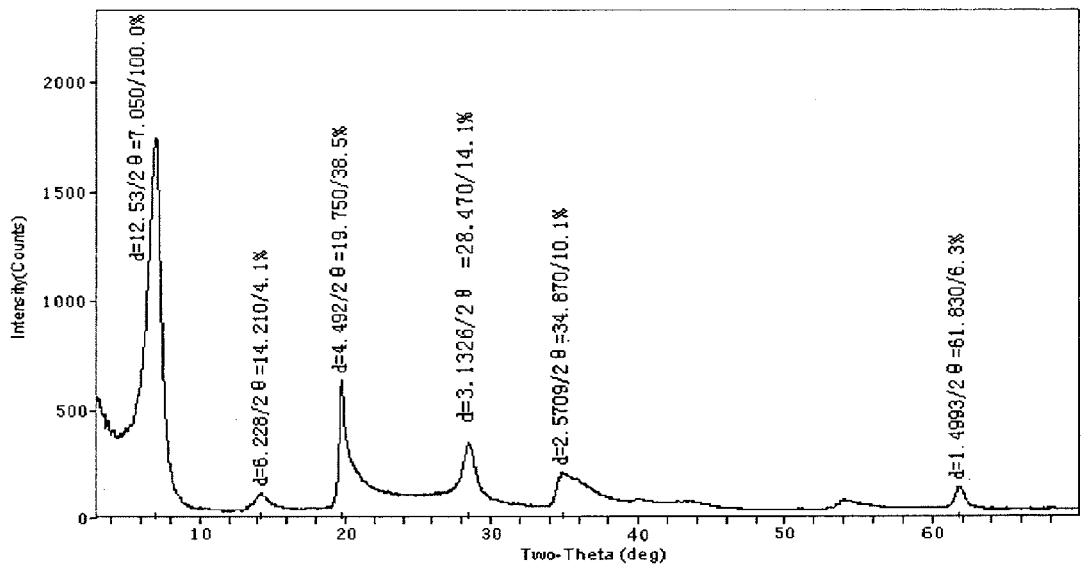
FIG. 7 is an X-ray powder diffraction spectrum of the modified sodium-montmorillonite A, which is prepared by the process disclosed in CN20068 0028247.8.

The obtained modified hydrogen-montmorillonite was formulated as a slurry with a solid content of 20% using 0.5N hydrochloric acid solution, and after being stirred for 6 h, filtered to remove the acid. The filter cake was washed with water at 60° C. to a pH value of about 5, then press-filtered to give a filter cake with a solid content of about 50%. Sodium carbonate was added in an amount equivalent to the cation exchange capacity (for example, 4.5-5% of the amount of the modified calcium-montmorillonite used). The mixture was then stirred to carry out sodium modification for 34 hours until the pH value reached 7-8. Then the mixture was dried at 120° C. and ground to 300-500 meshes to give modified sodium-montmorillonite A. Its X-ray powder diffraction spectrum is shown in FIG. 7.

Example 9

Preparation of Powder of Modified Sodium-Montmorillonite

| | |
|---|---|
| Modified sodium-montmorillonite B-1 | 1000 g |
| glucose | 2500 g |
| Made into | 1000 bags |

Preparation Process:

Prescribed amount of modified sodium-montmorillonite and prescribed amount of glucose were mixed homogenously and filled in aluminum-plastic laminated packing bags according to specifications to give powder of modified sodium-montmorillonite.

Example 10

Preparation of Granules of Modified Sodium-Montmorillonite

| | |
|---|---|
| Modified sodium-montmorillonite B-1 | 500 g |
| glucose | 800 g |
| 10% solution of povidone K-30 | 500 g |
| Made into | 1000 bags |

Preparation Process:

1) Prescribed amount of modified sodium-montmorillonite and prescribed amount of glucose were mixed homogenously as dry mixture.

2) Prescribed amount of povidone K-30 solution was added in the dry mixture prepared in step 1) and mixed homogenously to give soft material.

3) The soft material was made into wet granules with a sieve of 24 meshes. The granules were dried at 60° C. and granulated with a sieve of 20 meshes to give dry granules.

4) The dry granules were filled in aluminum-plastic laminated packing bags according to specifications to give granules of modified sodium-montmorillonite.

Example 11

Preparation of Capsules of Modified Sodium-Montmorillonite

| | |
|---|---|
| Modified sodium-montmorillonite B-1 | 1000 g |
| glucose | 200 g |
| 10% solution of povidone K-30 | 200 g |
| Made into | 1000 bags |

Preparation Process:

1) Prescribed amount of modified sodium-montmorillonite and prescribed amount of glucose were mixed homogenously as dry mixture.

2) To the dry mixture, prescribed amount of povidone K-30 solution was added to give a soft material via homogenous mixing.

3) The soft material was made into wet granules with a sieve of 24 meshes. The granules were dried at 60° C. and granulated with a sieve of 20 meshes to give dry granules.

4) The dry granules were filled in empty capsules according to specifications to give capsules of modified sodium-montmorillonite.

Example 12

Preparation of Enteric Capsules of Modified Sodium-Montmorillonite

| | |
|---|---|
| Modified sodium-montmorillonite B-1 | 500 g |
| glucose | 200 g |
| Made into | 1000 granules |

Preparation Process:

1) Prescribed amount of modified sodium-montmorillonite and prescribed amount of glucose were mixed homogenously as dry mixture.

2) The dry mixture was dried at 80° C. for 2 hours and then passed through a sieve of 80 meshes;

3) The dry powder mixture was filled in empty enteric capsules according to specifications to give enteric capsules of modified sodium-montmorillonite.

Example 13

Preparation of Gels of Modified Sodium-Montmorillonite

| | |
|---|---|
| Modified sodium-montmorillonite B-1 | 80 g |
| Benzoic acid | 0.1 g |
| Purified water | 1200 g |

Preparation Process:

1) Formulating amount of the raw materials and auxiliaries were weighted.

2) The modified sodium-montmorillonite was initially added in purified water and the mixture was mixed homogenously. Then benzoic acid was added and the obtained mixture was again mixed homogenously. The mixture thus obtained was sheared in a shearing machine for 15 minutes to give a gel.

3) The gel was boiled for 15 minutes for sterilization, then divided and packed to give gels of modified sodium-montmorillonite.

Example 14

Preparation of Effervescent Tablets of Modified Sodium-Montmorillonite

| | |
|---|---|
| Modified sodium-montmorillonite B-1 | 500 g |
| Sodium bicarbonate | 150 g |
| Citric acid | 50 g |
| Made into | 1000 tablets |

Preparation Process:

Prescribed amount of modified sodium-montmorillonite and prescribed amount of sodium bicarbonate and citric acid were mixed homogenously and tableted directly according to specifications to give effervescent tablets of modified sodium-montmorillonite.

The therapeutic use of the modified sodium-montmorillonite according to the invention can be verified by the following experimental examples. The physical and chemical parameters of montmorillonites used in the experiments are shown in table 2.

TABLE 2

Physical and chemical property parameters of natural montmorillonite and modified montmorillonite

| | Sample | | | | |
|---|---|---|---|---|---|
| Parameters | Natural calcium-montmorillonite | Natural sodium-montmorillonite | Modified calcium-montmorillonite | Modified sodium-montmorillonite A | Modified sodium-montmorillonite B-1 |
| Cation exchange capacity (mmol/100 g) | 110 | 89 | 128 | 130 | 135 |
| Adhesion (g/g) | 0.45 | 0.31 | 0.46 | 0.45 | 0.55 |

TABLE 2-continued

Physical and chemical property parameters of natural montmorillonite and modified montmorillonite

| Parameters | Sample | | | | |
|---|---|---|---|---|---|
| | Natural calcium-mont-morillonite | Natural sodium-mont-morillonite | Modified calcium-mont-morillonite | Modified sodium-mont-morillonite A | Modified sodium-mont-morillonite B-1 |
| Swelling capacity in intestinal juice (ml) | 7.0 | Pink semi gel | 12 | off-white suspension | off-white gel |
| Swelling capacity in gastric juice (ml) | 12.0 | Pink suspension | 21 | off-white suspension | off-white gel |
| $Ca^{2+}$ % (calculated as CaO) | 2.5 | 0.1 | 2.8 | 0.18 | 0.04 |
| $Na^+$ % (calculated as $Na_2O$) | 0.1 | 2.6 | 0.02 | 3.8 | 3.6 |
| Thixotropic index | 0 | 0.5 | 0.5 | 3 | 6 |

Experiment Example 1

Protective Effects of Modified Sodium-Montmorillonite B-1 Against Ethanol-Induced Injury in Gastric Mucosa of Rats The experiment was carried out according to the general requirements concerning acute gastric mucosal injury pharmacodynamics in "A collection of guidelines for preclinical investigations of new drugs (western medicine)", issued in July, 1993 by the Drug Administration Bureau of the Ministry of Health of the People's Republic of China.

1. Experimental Method

90 SD rats (SINO-BRITISH SIPPR-BK LAB. ANIMAL LTD. CO, SCXK Shanghai 2008-0016) having body weight ranging from 200 to 220 g, with male and female rats of equal number, were divided into the following 9 groups, with 10 in each group: model group (double distilled water 1 ml/100 g), positive group (sucralfate 300 mg/kg), natural calcium-montmorillonite (300 mg/kg) group, modified calcium-montmorillonite (300 mg/kg) group, natural sodium-montmorillonite (300 mg/kg) group, modified sodium-montmorillonite A (300 mg/kg) group, modified sodium-montmorillonite B-1 low dosage group (75 mg/kg), middle dosage group (150 mg/kg) and high dosage group (300 mg/kg). Rats of each group were administrated intragastrically with an administration volume of 1 ml/100 g.

Rats were fasting for 48 h after the first intragastric administration (the bottom of the cages was raised up to prevent them from feeding on dung). During that period, the rats were administrated intragastrically every 24 hours. 15 minutes after the last administration, rats were administered intragastrically with absolute alcohol (1 ml per rat). 1 hour after the model establishment, all the rats were killed and dissected. The stomachs were collected and cut along the greater curvature of stomach, then fixed in 1% formaldehyde solution for 10 minutes. The degree of injury was evaluated and indicated by ulcer index. The length of streak shaped injury was measured if it was more than 1 mm, every mm counting for 1 score. If the width was more than 1 mm, the score would be doubled. The total score was the ulcer index of the animal. The data were analyzed using t-test. The ulcer suppression rate was calculated by the following formula:

$$\text{Ulcer suppression rate} = \frac{(\text{Ulcer index of control group} - \text{Ulcer index of treated group})}{\text{Ulcer index of control group}} \times 100\%$$

2. Experimental Results

From the experimental results shown in table 3, it can be seen that after intragastric administration of absolute alcohol in empty stomach, the rats of the model group have serious injury in stomach mucosa. Sucralfate can significantly protect gastric mucosa and alleviate the injury induced by ethanol, with an ulcer suppression rate up to 54.5%. There is a highly significant difference between the sucralfate group and the model group ($P<0.01$). The test sample modified sodium-montmorillonite B-1 group can also effectively prevent gastric mucosa from injuring by ethanol. Compared with the model group, the 75 mg/kg dosage group has significant difference ($P<0.05$), and the 150 mg/kg dosage group and the 300 mg/kg dosage group have highly significant differences ($P<0.01$). The ulcer suppression rate is from 42.7 to 72.8%. The protective effect is correlated positively with dosage.

In the comparison of the modified sodium-montmorillonite B-1 group with the sucralfate group, it can be seen that the ulcer suppression rate of the 75 mg/kg dosage group is lower than that of the sucralfate group, and the ulcer suppression rates of the 150 mg/kg dosage group and the 300 mg/kg dosage group are higher than that of the sucralfate group. Between the 300 mg/kg dosage group and the sucralfate group, P is 0.079. The calcium-montmorillonite group has no significant difference as compared with the model group.

3. Experimental Conclusion

Modified sodium-montmorillonite B-1 has significant protective effect against ethanol-induced gastric mucosa injury in fasting rats. With dosages of 150 mg/kg and 300 mg/kg, the ulcer suppression rates are respectively more than 70%, and the protective effects on gastric mucosa are slightly better than sucralfate.

TABLE 3

Protective effects of modified sodium-montmorillonite B-1 against ethanol-induced gastric mucosa injury in rats ($\bar{x} \pm s$)

| Group | Dosage (mg/kg) | The number of animals | Ulcer index | Ulcer suppression rate (%) |
|---|---|---|---|---|
| Model group | 1(ml/100 g) | 10 | 110.3 ± 46.6 | / |
| sucralfate group | 300 | 10 | 54.0 ± 25.3** | 51.0 |
| Natural calcium-montmorillonite group | 300 | 10 | 102.5 ± 28.8 | 6.8 |
| Modified calcium-montmorillonite group | 300 | 10 | 98.3 ± 22.6 | 10.8 |
| Modified sodium-montmorillonite A group | 300 | 10 | 65.8 | 40.2 |
| Natural sodium-montmorillonite group | 300 | 10 | 88.2 | 19.8 |
| Modified sodium-montmorillonite B-1 group | 70 | 10 | 63.3 ± 33.5* | 42.7 |
| | 150 | 10 | 32.2 ± 26.8* | 70.7 |
| | 300 | 10 | 29.9 ± 19.0**# | 72.8 |

Compared with model group: *P < 0.05, **P < 0.01;
Compared with sucralfate group: #P = 0.079.

Experiment Example 2

Protective Effects of Modified Sodium-Montmorillonite B-1 Against Hydrochloric Acid-Induced Gastric Mucosa Injury in Rats The experiment was carried out according to the general requirements concerning acute gastric mucosal injury pharmacodynamics in "A collection of guidelines for preclinical investigations of new drugs (western medicine)", issued in July, 1993 by the Drug Administration Bureau of the Ministry of Health of the People's Republic of China.

1. Experimental Method

90 SD rats (SINO-BRITISH SIPPR-BK LAB. ANIMAL LTD. CO, SCXK Shanghai 2008-0016) having body weight ranging from 200 to 220 g, with male and female rats of equal number, were divided into the following 9 groups, with 10 in each group: model group (double distilled water 1 ml/100 g), positive group (sucralfate 300 mg/kg), natural calcium-montmorillonite (300 mg/kg) group, modified calcium-montmorillonite (300 mg/kg) group, natural sodium-montmorillonite (300 mg/kg) group, modified sodium-montmorillonite A (300 mg/kg) group, modified sodium-montmorillonite B-1 low dosage group (75 mg/kg), middle dosage group (150 mg/kg) and high dosage group (300 mg/kg). Rats of each group were administrated intragastrically with an administration volume of 1 ml/100 g.

Rats were fasting for 48 h after the first intragastric administration (the bottom of the cages was raised up to prevent them from feeding on dung). During that period, the rats were administrated intragastrically every 24 hours. 15 minutes after the last administration, rats were administered intragastrically with 0.6 mol/L of hydrochloric acid (1 ml per rat). 1 hour after the model establishment, all the rats were killed and dissected. The stomachs were collected and cut along the greater curvature of stomach, then fixed in 1% formaldehyde solution for 10 minutes. The degree of injury was evaluated and indicated by ulcer index. The length of streak shaped injury was measured if it was more than 1 mm, every mm counting for 1 score. If the width was more than 1 mm, the score would be doubled. The total score was the ulcer index of the animal. The data were analyzed using t-test. The ulcer suppression rate was calculated by the following formula:

$$\text{Ulcer suppression rate} = \frac{(\text{Ulcer index of control group} - \text{Ulcer index of treated group})}{\text{Ulcer index of control group}} \times 100\%$$

2. Experimental Results

See table 4.

TABLE 4

Protective effects of modified sodium-montmorillonite B-1 against hydrochloric acid-induced gastric mucosa injury in rats ($\bar{x} \pm s$)

| Group | Dosage (mg/kg) | The number of animals | Ulcer index | Ulcer suppression rate (%) |
|---|---|---|---|---|
| Model group | 1 (ml/100 g) | 10 | 48.0 ± 14.0 | / |
| sucralfate group | 300 | 10 | 8.4 ± 5.0** | 82.5 |
| Natural calcium-montmorillonite group | 300 | 10 | 45.8 ± 3.5 | 4.5 |
| Modified calcium-montmorillonite group | 300 | 10 | 42.6 ± 4.2 | 11.2 |
| Modified sodium-montmorillonite A group | 300 | 10 | 15.3 | 68.1 |
| Natural sodium-montmorillonite group | 300 | 10 | 37.6 | 21.7 |
| | 75 | 10 | 16.1 ± 8.3*### | 66.5 |

TABLE 4-continued

Protective effects of modified sodium-montmorillonite B-1 against hydrochloric acid-induced gastric mucosa injury in rats ($\bar{x} \pm s$)

| Group | Dosage (mg/kg) | The number of animals | Ulcer index | Ulcer suppression rate (%) |
|---|---|---|---|---|
| Modified sodium-montmorillonite B-1 group | 150 | 10 | 7.0 ± 3.3** | 85.4 |
| | 300 | 10 | 3.6 ± 3.2**# | 92.5 |

Compared with model group: *P < 0.05, **P < 0.01;
Compared with sucralfate group: #P < 0.05, ##P < 0.01.

From table 4, it can be seen that after intragastric administration of 0.6 mol/L of hydrochloric acid in empty stomach, the rats of the model group have serious injury in stomach mucosa, with an ulcer index of above 40. Sucralfate can significantly protect gastric mucosa and alleviate the injury induced by hydrochloric acid, with a ulcer suppression rate up to 82.5%. There is highly significant difference between the sucralfate group and the model group (P<0.01). The modified sodium-montmorillonite B-1 group can also effectively prevent gastric mucosa from injuring by hydrochloric acid. Compared with the control group, the 75 mg/kg dosage group has significant difference (P<0.05), the 150 mg/kg dosage group and the 300 mg/kg dosage group have highly significant differences (P<0.01). The protective effect is correlated positively with dosage.

In the comparison of the modified sodium-montmorillonite B-1 group with the positive drug sucralfate group, it can be seen that the ulcer index of the 75 mg/kg dosage group is highly significantly higher than that of the sucralfate group (P<0.01). The ulcer indexes of the 150 mg/kg dosage group and the 300 mg/kg dosage group are lower than that of the sucralfate group. There is a significant difference between the 300 mg/kg dosage group and the sucralfate group (P<0.05).

3. Experimental Conclusion

Modified sodium-montmorillonite B-1 has significant protective effect against gastric mucosa injury induced by 0.6 mol/L hydrochloric acid in fasting rats. With dosages of 150 mg/kg and 300 mg/kg, the ulcer suppression rates are respectively more than 80%, and the protective effect on gastric mucosa of the high dosage group is superior to that of the sucralfate group and the modified sodium-montmorillonite A group.

Experiment Example 3

Growth Inhibitory Effects of the Modified Sodium-Montmorillonite B-1 on *Helicobacter pylori* In Vitro 1. Samples, Agents and Methods
1.1 Samples Natural calcium-montmorillonite, natural sodium-montmorillonite, modified calcium-montmorillonite, modified sodium-montmorillonite A, modified sodium-montmorillonite B-1 and physiologic saline.

1.2 The Source of Bacteria and Culture Medium

*Helicobacter pylori* (HP) strain NCTC11637 and strain SS1. HP strains were Gram-negative and arc-shaped or seagull-shaped *bacillus* as shown by optical microscope. They showed positive results in rapid urease test.

Columbia agar (bioMérieux) containing 7% anticoagulant sheep blood was used as a culture medium, with 10 mg/L vancomycin (Sigma), 5 mg/L TMP (Sigma) and 5 mg/L amphotericin B (Sigma) being added. The bacteria were cultivated at 37° C. under an atmosphere comprising 75% $N_2$, 12% $CO_2$ and 8% $O_2$ for 4-5 days.

1.3 Determination of MIC

By the serial two-fold agar dilution method, natural calcium-montmorillonite, modified calcium-montmorillonite and natural sodium-montmorillonite in each case were formulated into medicinal solutions with a final concentration of 145 mg/ml, 72.5 mg/ml, 36.25 mg/ml, 18.13 mg/ml, 9.06 mg/ml or 4.53 mg/ml. Modified sodium-montmorillonite A and modified sodium-montmorillonite B-1 in each case were formulated into medicinal solutions with a final concentration of 80 mg/ml, 40 mg/ml, 20 mg/ml, 10 mg/ml, 5 mg/ml or 2.5 mg/ml.

Using McFarland's turbidimetry, fresh culture of each HP strain was formulated into a $1\times10^8$/ml suspension. In each case, 0.1 ml of the suspension was taken and mixed homogenously with one of the medicinal solutions with different dilution degrees. The mixtures were incubated at 37° C. for 30 minutes with continuous mixing. The mixtures were then centrifuged at 2000 rpm for 4 minutes. 0.01 ml of the supernatant was taken and inoculated on Columbia blood agar plate, and cultivated at 37° C. under an atmosphere comprising 85% $N_2$, 10% $CO_2$ and 5% $O_2$ for 4-5 days before observation of results. In the experiments, different controls were also set, including the direct inoculation controls in which the medicinal solutions with different dilution degrees were respectively mixed with bacteria suspension and the obtained mixtures were incubated but not centrifuged, and the normal HP controls in which the procedures of mixing, incubation, centrifugation and inoculation with the supernatant are carried out similarly except that no medicine was added.

2. Results

All of the direct inoculation controls and the normal HP controls showed growth of bacteria. There are great differences in the growth of HP among the groups in which different samples were mixed with the bacteria suspension and the obtained mixture were incubated and inoculated by using supernatant from centrifugation: natural calcium-montmorillonite with a concentration of 145 mg/ml can inhibit the growth of HP strains NCTC11637 and SS1, and its $MIC_{100}$ is 145 mg/ml; modified calcium-montmorillonite with a concentration of 145 mg/ml can inhibit the growth of HP strains NCTC11637 and SS1, and its $MIC_{100}$ is 123 mg/ml; natural sodium-montmorillonite with a concentration of 72.5 mg/ml can inhibit the growth of HP strains NCTC11637 and SS1, and its $MIC_{100}$ is 72.5 mg/ml; modified sodium-montmorillonite A with a concentration of not less than 20 mg/ml can inhibit the growth of HP strains NCTC11637 and SS1, and its $MIC_{100}$ is 20 mg/ml; modified sodium-montmorillonite B-1 with a concentration of not less than 2.5 mg/ml can inhibit the growth of HP strains NCTC11637 and SS1, and its $MIC_{100}$ is 2.5 mg/ml. The results are shown in table 5.

TABLE 5

Growth inhibitory effects of montmorillonite on Helicobacter pylori in vitro

| Group | Strain | MIC (mg/ml) The range of MIC | $MIC_{100}$ |
|---|---|---|---|
| Natural calcium-montmorillonite group | HP NCTC11637 | 145 | 145 |
| | HP SS1 | 145 | 145 |
| Modified calcium-montmorillonite group | HP NCTC11637 | 123 | 123 |
| | HP SS1 | 123 | 123 |
| Natural sodium-montmorillonite group | HP NCTC11637 | 72.5-145 | 72.5 |
| | HP SS1 | 72.5-145 | 72.5 |
| Modified sodium-montmorillonite A group | HP NCTC11637 | 20-50 | 20 |
| | HP SS1 | 20-50 | 20 |
| Modified sodium-montmorillonite B-1 group | HP NCTC11637 | 2.5-50 | 2.5 |
| | HP SS1 | 2.5-50 | 2.5 |
| Physiologic Saline group* | HP NCTC11637 | / | / |
| | HP SS1 | / | / |

/: no inhibitory effect

From table 5, it can be seen that, compared with natural sodium-montmorillonite, natural calcium-montmorillonite, modified sodium-montmorillonite A and modified calcium-montmorillonite, the modified sodium-montmorillonite B-1 has excellent inhibitory effect on *Helicobacter pylori* and has significant difference.

3. Conclusions

After mixed with bacteria suspension, incubated and inoculated by using supernatant from centrifugation, natural calcium-montmorillonite, modified calcium-montmorillonite and natural sodium-montmorillonite can inhibit the growth of HP strains NCTC11637 and SS1, with $MIC_{100}$ of 145 mg/ml, 123 mg/ml and 72.5 mg/ml, respectively. Modified sodium-montmorillonite A and modified sodium-montmorillonite B-1 can significantly inhibit the growth of HP strains NCTC11637 and SS1, with $MIC_{100}$ and $MIC_{90}$ of 20 mg/ml and 2.5 mg/ml, respectively. Saline, however, has no inhibitory effect on each HP strain.

Experiment Example 4

Reversal Therapeutic Effect of Modified Sodium-Montmorillonite B-1 on Chronic Atrophic Gastritis 80 healthy and mature male SD rats of 8-week aged (Experimental Animal Center of Zhejiang Province, SCXK Zhe 2003-0001), with an average body weight of 250 g±50 g, were caged in a battery at a temperature of 24±2° C. in a humidity of 55±5% under 12-hour light/12-hour dark cycle condition, and fed on mixed feed.

To establish CAG model, 60% alcohol, 20 mmol/L sodium deoxycholate and 0.1% aqueous ammonia were administrated in combination for 24 weeks according to Si-Shi modeling method. Specifically, the rats were intragastrically administrated with 20 mmol/L of sodium deoxycholate every day, with fasting on Tuesday and Friday (the feed was taken away at 9:00 p.m. on Monday and Thursday, and the rats were intragastrically administrated with fasting at 9:00 a.m. in next morning). The dosage was as follows: for a rat with a body weight of <200 g, 1 ml was intragastrically administrated each time; for a rat with a body weight of 200-250 g, 1.5 ml was intragastrically administrated each time; and for a rat with a body weight of >250 g, 2 ml was intragastrically administrated each time. 60% alcohol was intragastrically administrated with fasting on Tuesday and Friday under the same condition and dosage as sodium deoxycholate. 0.1% aqueous ammonia was given freely, with its amount being recorded. The rats were killed after 24 weeks.

80 SD rats were divided into the following 8 groups, with 10 in each group: model group, physiologic saline group (placebo control group), sucralfate group, natural calcium-montmorillonite group, modified calcium-montmorillonite group, natural sodium-montmorillonite group, modified sodium-montmorillonite A group, and modified sodium-montmorillonite B-1 group. In the model group, after rat CAG model establishment, the rats were killed at the weekend of $24^{th}$ week. In the physiologic saline group, after rat CAG model establishment, simulation was stopped and physiologic saline was intragastrically administrated once a day, and the rats were killed at the weekend of $28^{th}$ week. In the sucralfate group, after rat CAG model establishment, simulation was stopped and sucralfate suspension (100 mg/mL) was intragastrically administrated with the following dosage: for a rat with a body weight of <200 g, 1 ml was intragastrically administrated per rat each time; for a rat with a body weight of 200-250 g, 1.5 ml was intragastrically administrated per rat each time; and for a rat with a body weight of >250 g, 2 ml was intragastrically administrated per rat each time. In the natural calcium-montmorillonite group, the modified calcium-montmorillonite group, the natural sodium-montmorillonite group, the modified sodium-montmorillonite A group and the modified sodium-montmorillonite B group, after rat CAG mold establishment, simulation was stopped and the modified sodium-montmorillonite A, natural calcium-montmorillonite and natural sodium-montmorillonite suspension (100 mg/mL) were intragastrically administrated respectively with the following dosage: for a rat with a body weight of <200 g, 1 ml was intragastrically administrated per rat each time; for a rat with a body weight of 200-250 g, 1.5 ml was intragastrically administrated per rat each time; and for a rat with a body weight of >250 g, 2 ml was intragastrically administrated per rat each time. In the modified sodium-montmorillonite B1 group, dosage regimen was the same as that of the sucralfate group, i.e. after rat CAG mold establishment, simulation was stopped and the modified sodium-montmorillonite B1 suspension (50 mg/mL) was intragastrically administrated with the following dosage: for a rat with a body weight of <200 g, 1 ml was intragastrically administrated per rat each time; for a rat with a body weight of 200-250 g, 1.5 ml was intragastrically administrated per rat each time; and for a rat with a body weight of >250 g, 2 ml was intragastrically administrated per rat each time. The rats were killed at the weekend of $28^{th}$ week.

24 hours after fasting but drinking water, the rats were fixed by being intraperitoneally anaesthetized with 1% pentobarbitone (40 mg/kg). The rats were dissected immediately with the whole stomach exposed. The whole stomach was taken at 1.5 cm from cardia and pylorus, cut along the greater curvature of stomach, washed with ice-cold physiologic saline, and spreaded after the moisture was absorbed by a filter paper. Gastric mucosa was taken from a half of gastric antrum with a glass slide, frozen with liquid nitrogen and stored at −70° C. The rest of the gastric mucosa specimen was fixed with 10% neutral formaldehyde solution. A streak shape sample was collected along the greater curvature of stomach, dehydrated conventionally and embedded with paraffin. Then the sample was cut into slices continuously with a thickness of 5 μm, placed on a slide which had been subjected to anti-escaping treatment with poly-L-lysine and stained with hematoxylin-eosin (HE). Gastric mucosa inflammation of each group was evaluated by semi-quantitative method. The full gastric mucosa was observed under low power microscope, each gastric mucosa being observed in gastric antrum and gastric body with 10 vision fields. The degree of inflammatory cell invasion was divided into seven grades of 0, 0.5, 1.0, 1.5, 2.0, 2.5, 3.0 according to Diagnostic Criterion of Gastritis issued in Houston, American in 1994. The inflammation degree of the 10 vision fields was recorded using above method, and averaged to give the inflammation index of gastric antrum and gastric body in every rat.

Figure 11:
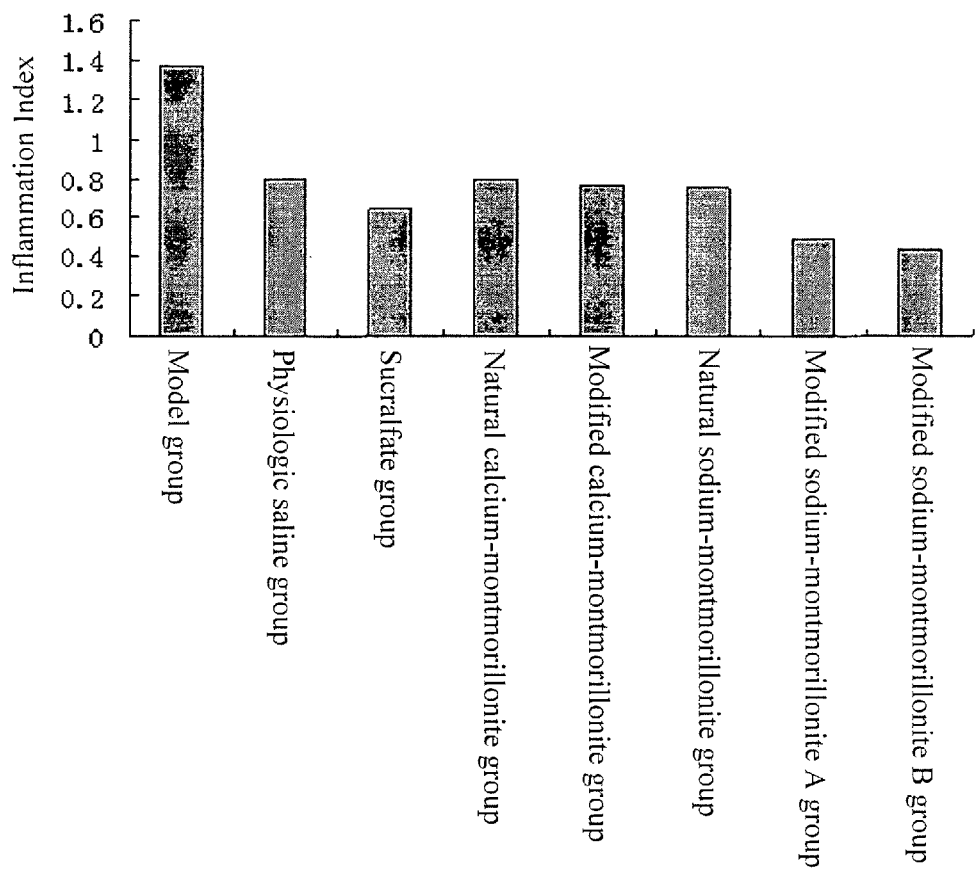
FIG. 11 is the effects of each experimental sample on rat antral gastritis index.

The experimental results are analyzed using analysis of variance of completely random design (One-Way ANOVA) by SPSS11.0 statistic software. The results are shown in FIG. 11. It can be seen that in terms of the inflammation index of gastric antrum mucosa in rats, montmorillonite treatment group is significantly better than CAG model control group and placebo control group; the modified sodium-montmorillonite B-1 group and the modified sodium-montmorillonite A group are significantly better than the sucralfate group ($P<0.05$); and the modified sodium-montmorillonite B-1 group is better than the modified sodium-montmorillonite A group ($P<0.05$), and highly significantly better than the natural montmorillonite groups ($P<0.01$).

What is claimed is:

1. A modified sodium-montmorillonite, wherein the content of $Na^+$ In the modified sodium-montmorillonite, calculated as $Na_2O$, is not less than 2%, and the thixotropic index of the modified sodium-montmorillonite is not less than 4, and
wherein the modified sodium-montmorillonite is prepared by a method comprising
 1) mixing montmorillonite with a purity of not less than 90% and 0.1-10 mol/L of an acid in a weight ratio of 1:1-100, followed by adding 0.05-3.5% of a dispersing agent based on the weight of the montmorillonite, boiling the mixture to remove the acid and washing to give a liquid dispersion of modified hydrogen-montmorillonite; and
 2) controlling the solid content of the liquid dispersion of the modified hydrogen-montmorillonite obtained from 1) within 0.5-10% and adding an sodium modification agent in an amount of not less than the cation exchange capacity of the montmorillonite in order to subject the montmorillonite to sodium modification,
wherein the content of $Ca^{2+}$ in the modified sodium-montmorillonite, calculated as CaO, is not more than 0.04%.

2. The modified sodium-montmorillonite according to claim 1, wherein the d-value corresponding to $d_{002}$ peak in the X-ray powder diffraction spectrum of the modified sodium-montmorillonite is 5.50 Å-7.00 Å.

3. The modified sodium-montmorillonite according to claim 1, wherein the purity of the modified sodium-montmorillonite is not less than 97%.

4. The modified sodium-montmorillonite according to claim 1, wherein the adsorption of strychnine sulfate by per gram of the modified sodium-montmorillonite is 0.30-0.75 g.

5. The modified sodium-montmorillonite according to claim 1, wherein the swelling capacity of the modified sodium-montmorillonite is not less than 7.0 ml/g.

6. The modified sodium-montmorillonite according to claim 1, wherein the content of heavy metal in the modified sodium-montmorillonite is not more than 10 ppm.

* * * * *